(12) United States Patent
Kudo

(10) Patent No.: US 10,383,723 B2
(45) Date of Patent: Aug. 20, 2019

(54) INTRAOCULAR LENS INJECTOR AND INTRAOCULAR LENS INJECTION DEVICE

(71) Applicant: HOYA CORPORATION, Tokyo (JP)

(72) Inventor: Kazunori Kudo, Saku (JP)

(73) Assignee: Hoya Corporation, Tokyo (JP)

( * ) Notice: Subject to any disclaimer, the term of this patent is extended or adjusted under 35 U.S.C. 154(b) by 81 days.

(21) Appl. No.: 15/126,277

(22) PCT Filed: Dec. 18, 2014

(86) PCT No.: PCT/JP2014/083510
§ 371 (c)(1),
(2) Date: Sep. 14, 2016

(87) PCT Pub. No.: WO2015/141085
PCT Pub. Date: Sep. 24, 2015

(65) Prior Publication Data
US 2017/0079772 A1    Mar. 23, 2017

(30) Foreign Application Priority Data
Mar. 19, 2014 (JP) ................................ 2014-055761

(51) Int. Cl.
*A61F 2/16* (2006.01)

(52) U.S. Cl.
CPC .......... *A61F 2/1667* (2013.01); *A61F 2/1675* (2013.01); *A61F 2/1678* (2013.01)

(58) Field of Classification Search
CPC ........ A61F 9/00; A61F 2/1664; A61F 2/1667; A61F 9/0008; A61F 2/148; A61F 2/1662–1678
See application file for complete search history.

(56) References Cited

U.S. PATENT DOCUMENTS 3,212,685 A   10/1965 Swan
4,877,026 A * 10/1989 de Laforcade ...............................
                                              A61B 17/320016
                                              606/171
(Continued)

FOREIGN PATENT DOCUMENTS

DE   19544119 A1   5/1997
EP    2074961 A1   7/2009
(Continued)

OTHER PUBLICATIONS

PCT Search Report dated Mar. 31, 2015 for PCT App. Ser. No. PCT/JP2014/083510.
(Continued)

*Primary Examiner* — Shaun L David
*Assistant Examiner* — Brigid K Byrd
(74) *Attorney, Agent, or Firm* — Henricks Slavin LLP

(57) ABSTRACT

An intraocular lens injector (1) includes: a hollow body having an injector body (5) provided with a lens placement portion (11) on which an intraocular lens is placed, and a screw member (8) with a first threaded portion (8*b*) formed thereon and connected to a rear end portion of the injector body (5), and rotatable around an axis of the injector body (5) without moving in an axial direction of the injector body; and a moving member (9, 10) having a second threaded portion (9*c*) that engages with the first threaded portion (8*b*) from an initial state before use, and configured to release the intraocular lens from a tip of an injection tube 7 by moving in an axial direction of the injector body (5) independently from the screw member (8) due to an engagement of the first threaded portion (8*b*) and the second threaded portion (9*c*), during a rotating operation of the screw member (8).

20 Claims, 25 Drawing Sheets

(56) References Cited

U.S. PATENT DOCUMENTS

| | | | | |
|---|---|---|---|---|
| 4,919,130 | A | * | 4/1990 | Stoy ............... A61F 2/1664 606/107 |
| 5,222,972 | A | * | 6/1993 | Hill ............... A61F 2/1664 606/107 |
| 5,728,075 | A | * | 3/1998 | Levander ............ A61M 5/2448 604/211 |
| 5,807,400 | A | * | 9/1998 | Chambers ............ A61F 2/1664 606/107 |
| 6,050,999 | A | * | 4/2000 | Paraschac ............ A61F 2/148 219/636 |
| 6,251,114 | B1 | * | 6/2001 | Farmer ............... A61F 2/1664 606/107 |
| 6,386,357 | B1 | * | 5/2002 | Egawa ............... A61F 2/1664 206/5.1 |
| 8,475,526 | B2 | * | 7/2013 | Pynson ............... A61F 2/167 623/6.12 |
| 9,554,894 | B2 | | 1/2017 | Inoue |
| 9,572,710 | B1 | | 2/2017 | Kudo et al. |
| 9,610,195 | B2 | * | 4/2017 | Horvath ............ A61F 9/00781 |
| 9,655,718 | B2 | | 5/2017 | Kudo |
| 9,687,340 | B2 | * | 6/2017 | Anderson ............... A61F 2/167 |
| 9,877,826 | B2 | | 1/2018 | Kudo et al. |
| 9,901,442 | B2 | | 2/2018 | Kudo et al. |
| 9,907,647 | B2 | | 3/2018 | Inoue |
| 9,980,811 | B2 | | 5/2018 | Kudo et al. |
| 10,039,668 | B2 | | 8/2018 | Kudo et al. |
| 2001/0007075 | A1 | * | 7/2001 | Hjertman ............ A61F 2/1667 606/107 |
| 2002/0151904 | A1 | * | 10/2002 | Feingold ............ A61F 2/1664 606/107 |
| 2004/0147938 | A1 | * | 7/2004 | Dusek ............... A61F 2/1664 606/107 |
| 2007/0270945 | A1 | | 11/2007 | Kobayashi |
| 2008/0097459 | A1 | * | 4/2008 | Kammerlander ..... A61F 2/1664 606/107 |
| 2009/0036898 | A1 | * | 2/2009 | Ichinohe ............ A61F 2/1678 606/107 |
| 2009/0270876 | A1 | | 10/2009 | Hoffmann et al. |
| 2010/0094309 | A1 | * | 4/2010 | Boukhny ............ A61F 2/1662 606/107 |
| 2010/0185206 | A1 | * | 7/2010 | Ichinohe ............ A61F 2/1672 606/107 |
| 2010/0286704 | A1 | * | 11/2010 | Ichinohe ............ A61F 2/1667 606/107 |
| 2011/0172676 | A1 | * | 7/2011 | Chen ............... A61F 2/1662 606/107 |
| 2011/0288557 | A1 | * | 11/2011 | Kudo ............... A61F 2/167 606/107 |
| 2012/0022549 | A1 | * | 1/2012 | Someya ............... A61F 2/1678 606/107 |
| 2012/0123438 | A1 | * | 5/2012 | Horvath ............ A61F 9/00781 606/108 |
| 2013/0006259 | A1 | * | 1/2013 | Sanger ............... A61F 2/1672 606/107 |
| 2013/0226193 | A1 | * | 8/2013 | Kudo ............... A61F 2/148 606/107 |
| 2013/0345713 | A1 | * | 12/2013 | Cole ............... A61F 2/1664 606/107 |
| 2014/0276901 | A1 | * | 9/2014 | Auld ............... A61F 2/1678 606/107 |
| 2015/0327992 | A1 | | 11/2015 | Wagner et al. |
| 2016/0270907 | A1 | | 9/2016 | Attinger |
| 2016/0331587 | A1 | | 11/2016 | Yamada et al. |
| 2016/0346077 | A1 | | 12/2016 | Someya et al. |
| 2017/0151056 | A1 | | 6/2017 | Inoue |
| 2017/0172676 | A1 | | 6/2017 | Itkowitz et al. |
| 2017/0202662 | A1 | | 7/2017 | Someya et al. |
| 2017/0252149 | A1 | | 9/2017 | Kudo et al. |
| 2017/0252150 | A1 | | 9/2017 | Kudo et al. |
| 2017/0258582 | A1 | | 9/2017 | Kudo et al. |
| 2017/0354493 | A1 | * | 12/2017 | Andersen ............... A61F 2/167 |
| 2018/0250125 | A1 | | 9/2018 | Kudo et al. |
| 2018/0353287 | A1 | | 12/2018 | Kudo et al. |

FOREIGN PATENT DOCUMENTS

| | | |
|---|---|---|
| JP | 2007-244570 A | 9/2007 |
| JP | 2007-307168 A1 | 11/2007 |
| JP | 2016-137122 A | 8/2016 |

OTHER PUBLICATIONS

U.S. Appl. No. 14/812,104, filed Jul. 29, 2015, US 20160113759A1.
U.S. Appl. No. 15/071,880, filed Mar. 16, 2016, US 20160193038A1.
U.S. Appl. No. 15/608,895, filed May 30, 2017, US 20170258582A1.
U.S. Appl. No. 15/600,679, filed May 19, 2017, US 20170252149A1.
U.S. Appl. No. 15/600,684, filed May 19, 2017, US 20170252150A1.
EPO Extended European Search Report dated Oct. 17, 2017 for EPO App. Ser. No. 14886062.0.
U.S. Appl. No. 12/602,442, filed Dec. 15, 2009, U.S. Pat. No. 8,747,465.
U.S. Appl. No. 13/244,449, filed Sep. 24, 2011, U.S. Pat. No. 9,289,288.
U.S. Appl. No. 15/063,395, filed Mar. 7, 2016, US 20160346077A1.
U.S. Appl. No. 15/476,717, filed Mar. 31, 2017, US 20170202662A1.
U.S. Appl. No. 12/602,454, filed Dec. 15, 2009, U.S. Pat. No. 8,475,528.
U.S. Appl. No. 13/244,452, filed Sep. 24, 2011, U.S. Pat. No. 8,535,375.
U.S. Appl. No. 12/667,510, filed Dec. 31, 2009, U.S. Pat. No. 9,114,006.
U.S. Appl. No. 14/812,104, filed Jul. 29, 2015, U.S. Pat. No. 9,907,647.
U.S. Appl. No. 12/995,263, filed Dec. 15, 2010, U.S. Pat. No. 9,554,894.
U.S. Appl. No. 15/382,377, filed Dec. 16, 2016, US 20170151056A1.
U.S. Appl. No. 12/997,651, filed Dec. 13, 2010, U.S. Pat. No. 8,382,769.
U.S. Appl. No. 13/757,790, filed Feb. 2, 2012, U.S. Pat. No. 9,186,246.
U.S. Appl. No. 13/583,216, filed Apr. 6, 2011, U.S. Pat. No. 9,326,847.
U.S. Appl. No. 13/699,708, filed Jun. 8, 2011, U.S. Pat. No. 8,647,382.
U.S. Appl. No. 14/145,846, filed Dec. 31, 2013, U.S. Pat. No. 9,314,373.
U.S. Appl. No. 15/071,880, filed Mar. 16, 2016, U.S. Pat. No. 10,039,668.
U.S. Appl. No. 15/336,678, filed Oct. 27, 2016, U.S. Pat. No. 9,572,710.
U.S. Appl. No. 15/608,895, filed May 30, 2017, U.S. Pat. No. 9,980,811.
U.S. Appl. No. 13/059,401, filed Feb. 16, 2011, U.S. Pat. No. 8,702,795.
U.S. Appl. No. 13/061,143, filed Feb. 26, 2011, U.S. Pat. No. 8,470,032.
U.S. Appl. No. 13/143,322, filed Jul. 5, 2011, U.S. Pat. No. 8,603,103.
U.S. Appl. No. 14/099,989, filed Dec. 8, 2013, U.S. Pat. No. 9,655,718.
U.S. Appl. No. 15/600,679, filed May 19, 2017, U.S. Pat. No. 9,877,826.
U.S. Appl. No. 15/600,684, filed May 19, 2017, U.S. Pat. No. 9,901,442.
U.S. Appl. No. 11/814,508, filed Jul. 23, 2007, U.S. Pat. No. 8,545,512.
U.S. Appl. No. 14/033,888, filed Sep. 23, 2013, U.S. Pat. No. 9,220,593.
U.S. Appl. No. 11/816,676, filed Aug. 20, 2007, U.S. Pat. No. 8,523,877.
U.S. Appl. No. 13/966,209, filed Aug. 13, 2013, U.S. Pat. No. 9,364,320.
U.S. Appl. No. 12/095,172, filed May 28, 2008, U.S. Pat. No. 8,523,941.
U.S. Appl. No. 14/011,018, filed Aug. 27, 2013, U.S. Pat. No. 8,968,328.

(56) References Cited

OTHER PUBLICATIONS

U.S. Appl. No. 12/088,328, filed Mar. 27, 2008, U.S. Pat. No. 8,574,239.
U.S. Appl. No. 14/065,365, filed Oct. 28, 2013, U.S. Pat. No. 9,114,007.
U.S. Appl. No. 11/722,601, filed Apr. 10, 2008, U.S. Pat. No. 8,460,311.
U.S. Appl. No. 15/126,277, filed Sep. 14, 2016, US 20170079772A1.
U.S. Appl. No. 15/756,565, filed Feb. 28, 2018, US 20180250125A1.
U.S. Appl. No. 15/756,569, filed Feb. 28, 2018, US 20180353287A1.
U.S. Appl. No. 16/313,180, filed Dec. 26, 2018.
U.S. Appl. No. 16/313,184, filed Dec. 26, 2018.

\* cited by examiner

INTRAOCULAR LENS INJECTOR AND INTRAOCULAR LENS INJECTION DEVICE

CROSS-REFERENCE TO RELATED APPLICATIONS

This application is the U.S. National Stage of PCT App. Ser. No. PCT/JP2014/083510, filed Dec. 18, 2014.

TECHNICAL FIELD

The present invention relates to an intraocular lens injector used for injecting an intraocular lens into an eye, and an intraocular lens injection device having the same.

DESCRIPTION OF RELATED ART

In a cataract surgery, removal of a cloudy lens by phacoemulsification, and an implantation into an eye after removal of the lens, are generally performed. Then, at present, a soft intraocular lens made of a soft material such as silicone elastomer or soft acryl, etc., is injected into an eye using an intraocular lens injector. As this type of the intraocular lens injector, for example, the intraocular lens injector disclosed in patent documents 1 and 2 is known.

In the intraocular lens injector disclosed in patent document 1, a threaded portion (female screw) is formed on an inner peripheral surface of a screw member, and a threaded portion (male screw) is formed on an outer peripheral surface of the injector body corresponding to the female screw. An injection tube is provided on a tip portion of the injector body. Further, a plunger is inserted into the screw member, and a rod is connected to the plunger. Then, in an initial state before using the intraocular lens injector, the threaded portion of the screw member and the threaded portion of the injector body are set in separated states without engaging the threaded portion of the screw member and the threaded portion of the injector body with each other. When the intraocular lens injector is actually used, in order to engage the threaded portion of the screw member and the threaded portion of the injector body, the screw member is pushed-in toward the injector body. Next, by rotating the screw member, the plunger is moved in an axial direction of the injector body by an engagement of the threaded portions, together with the screw member. At this time, a tip of the rod that moves together with the plunger, is brought into contact with the intraocular lens, and the intraocular lens is pushed-in in this state, to thereby release the intraocular lens from the tip of the injection tube.

PRIOR ART DOCUMENT

Patent Document

Patent document 1: Japanese Patent Laid Open Publication No. 2011-255029
Patent document 2: Japanese Unexamined Patent Application Publication No. 2007-533379

SUMMARY OF THE INVENTION

Problem to be Solved by the Invention

However, in the intraocular lens injector disclosed in patent document 1, the threaded portions are sometimes not engaged with each other smoothly when the screw member is pushed toward the injector body side. Therefore, when starting a rotation of the screw member, the threaded portions are disengaged instantaneously, a vibration or an impact occurs, thus possibly causing a shift of a position of the intraocular lens from a normal position. Further, when the screw member is pushed, the vibration, etc., occurs due to a collision between members, thus causing a similar problem.

The intraocular lens injector is configured to push the intraocular lens placed on a lens placement portion of the injector body, by the abovementioned tip of the rod. Therefore, if the position of the intraocular lens is shifted from the normal position, the intraocular lens is properly folded when the intraocular lens is pushed by the tip of the rod, and clogging, etc., is likely to occur. Especially, a positional deviation of the intraocular lens is likely to cause the clogging, etc., in the intraocular lens injector of a type of placing the intraocular lens made of a soft material on the lens placement portion of the injector body, and making the intraocular lens in a small folded state, thereby deforming the intraocular lens in a prescribed shape, and thereafter pushing out the intraocular lens by the tip of the rod by moving the plunger.

Further, the intraocular lens injector disclosed in patent document 2 is configured to engage the treaded portion formed on a first operation member, and the threaded portion formed on a second operation member, by pushing the first operation member. Therefore, the similar problem as described above possibly occurs.

A main object of the present invention is to provide an intraocular lens injector in which a vibration, etc., hardly occurs during operation compared to a conventional one during use of the intraocular lens injector, and an intraocular lens injection device including the intraocular lens injector.

Means for Solving the Problem

According to a first aspect of the present invention, there is provided an intraocular lens injector, including:
a hollow body having an injector body provided with a lens placement portion on which an intraocular lens is placed, and a rotating member with a first threaded portion formed thereon and connected to a rear end portion of the injector body, and rotatable around an axis of the injector body without moving in an axial direction of the injector body; and
a moving member having a second threaded portion that engages with the first threaded portion from an initial state before use, and configured to release the intraocular lens from a tip of the hollow body by moving in an axial direction of the injector body independently from the rotating member due to an engagement of the first threaded portion and the second threaded portion, when the rotating member is rotary-operated.

According to a second aspect of the present invention, there is provided the intraocular lens injector of the first aspect, wherein the moving member is housed in an interior of the hollow body without protruding from a rear end of the rotating member in the initial state before use, and configured to move in the interior of the hollow body when the rotating member is rotary-operated.

According to a third aspect of the present invention, there is provided the intraocular lens injector of the first or the second aspect, having a reverse rotation prevention mechanism for preventing a reverse rotation of the rotating member in the initial state before use.

According to a fourth aspect of the present invention, there is provided the intraocular lens injector of any one of the first to third aspects, wherein an intraocular lens is placed on the lens placement portion.

According to a fifth aspect of the present invention, there is provided the intraocular lens injector of any one of the first to fourth aspects, including:

a slider provided movably in an axial direction of the injector body, and configured to deform the intraocular lens into a prescribed shape, by abutting on the intraocular lens when moving it in one of the axial directions of the injector body; and a reverse return prevention mechanism configured to prevent a reverse return of the slider, when the slider is moved in one of the axial directions of the injector body.

According to a sixth aspect of the present invention, there is provided an intraocular lens injection device, including:

the intraocular lens injector of claim 5;

a case configured to house the intraocular lens injector; and a takeout prevention mechanism configured to prevent takeout of the intraocular lens injector from the case, in a state of housing the intraocular lens injector in the case, wherein when the slider is moved in one of the axial directions of the injector body in the state of housing the intraocular lens injector in the case, a takeout prevention state of the intraocular lens injector by the takeout prevention mechanism is canceled.

Advantage of the Invention

According to the present invention, the vibration, etc., hardly occurs during operation compared to a conventional one, when using the intraocular lens injector. Therefore, occurrence of a defective shape and clogging, etc., of the intraocular lens caused by the vibration, etc., during operation, is suppressed.

DETAILED DESCRIPTION OF THE INVENTION

Figure 1:
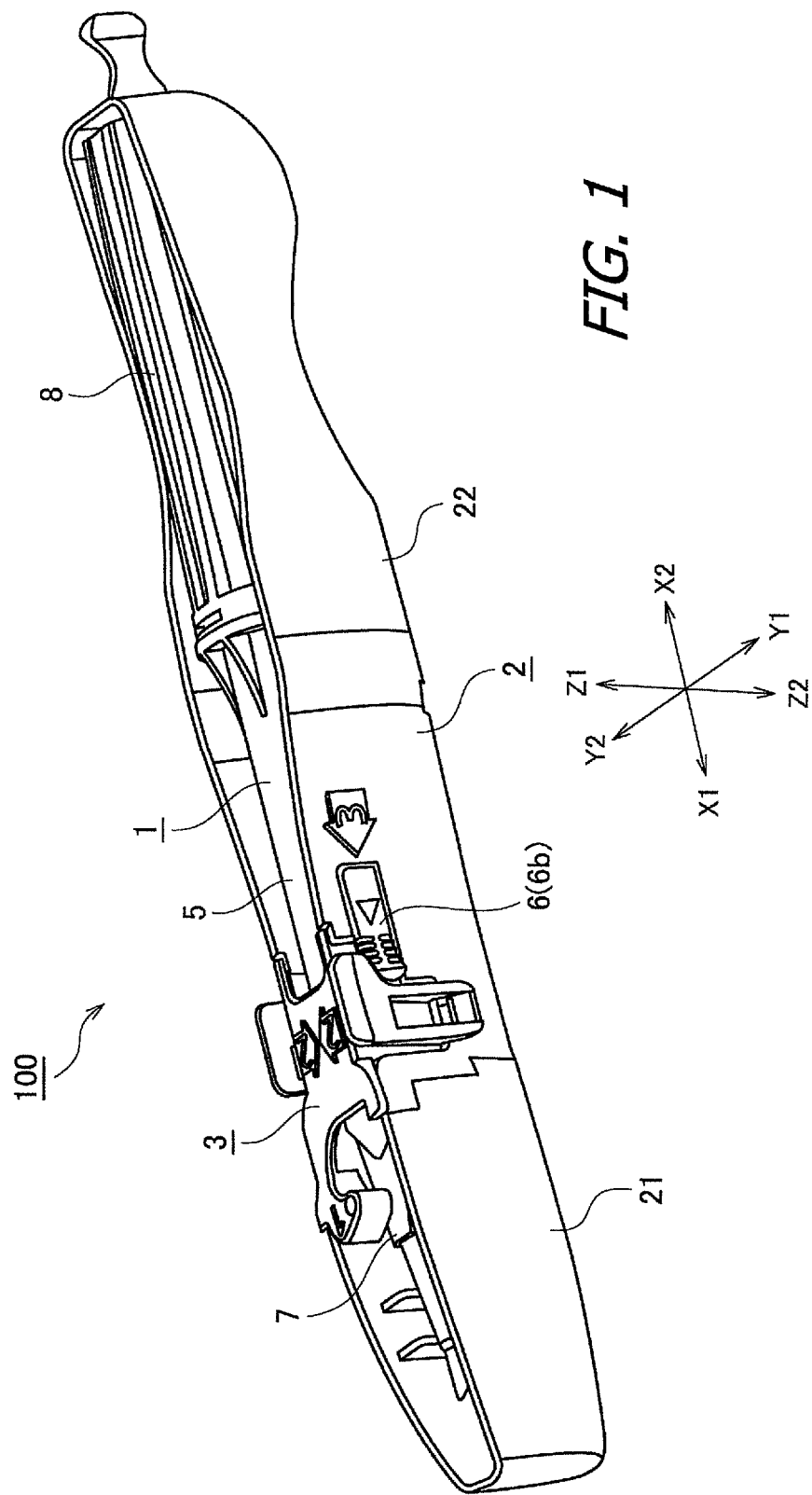
FIG. 1 is a perspective view illustrating a configuration of an intraocular lens injection device according to an embodiment of the present invention.

Embodiments of the present invention will be described hereafter, with reference to the drawings. The embodiments of the present invention will be described in the following order.

1. Configuration of an intraocular lens injection device
2. Configuration of an intraocular lens injector
3. Assembly method of the intraocular lens injection device
4. Use method of the intraocular lens injection device
5. Effect of the embodiment
6. Modified example, etc.

1. Configuration of an Intraocular Lens Injection Device

Figure 2:
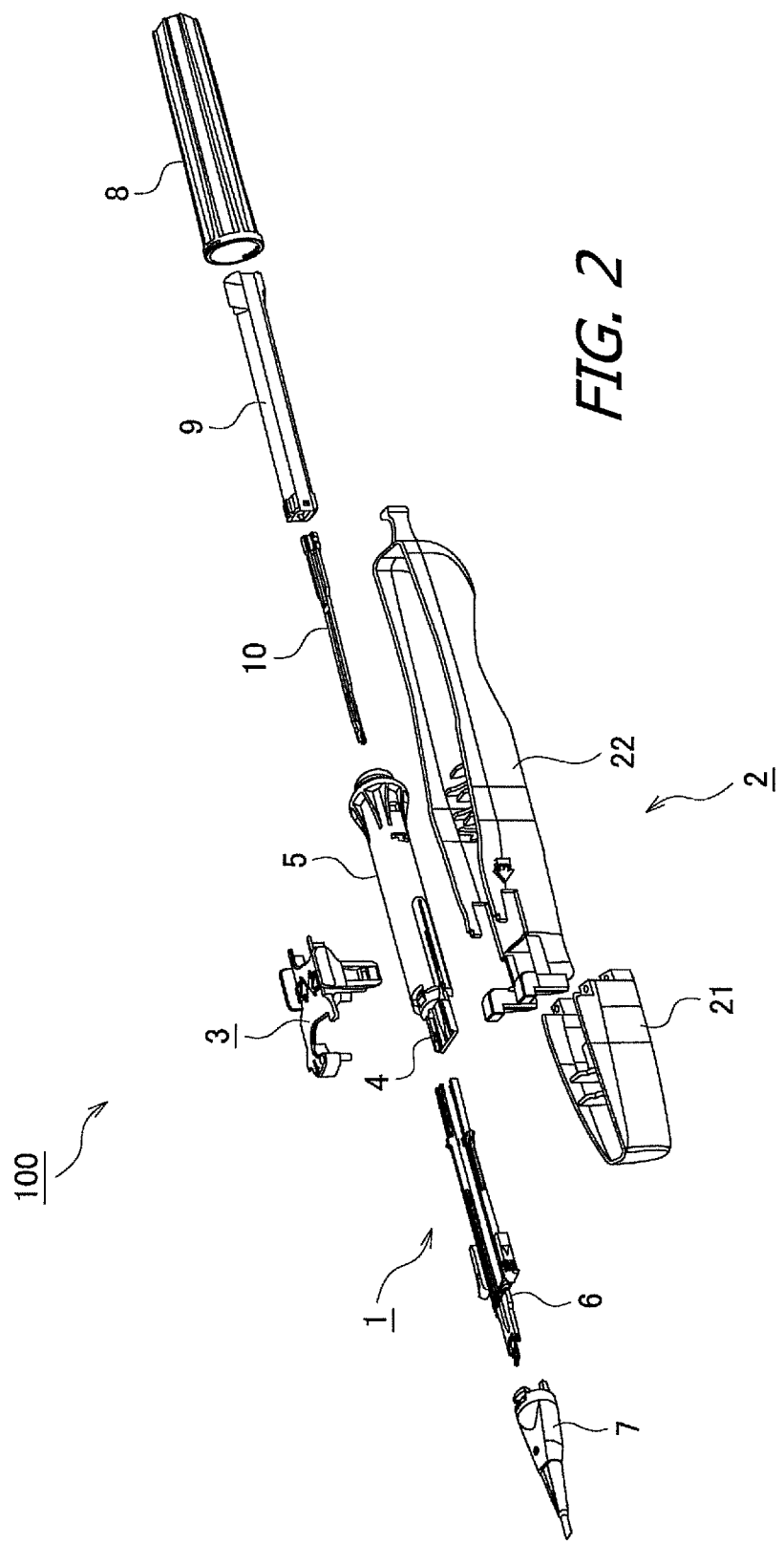
FIG. 2 is an exploded perspective view illustrating the configuration of the intraocular lens injection device according to an embodiment of the present invention.

FIG. 1 is a perspective view illustrating the configuration of the intraocular lens injection device according to an embodiment of the present invention, and FIG. 2 is an exploded perspective view illustrating the configuration of the intraocular lens injection device according to an embodiment of the present invention.

An intraocular lens injection device 100 has a configuration roughly including an intraocular lens injector 1, a case 2 for housing the intraocular lens injector 1 therein, and a case cover 3. These configuration members are made of synthetic resin respectively, and can be obtained by an integral molding of resin. However, each configuration member is configured by suitably combining a plurality of components (integral molding of resin) excluding the case cover 3. By thus configuring an entire body of the intraocular lens injection device 100 by synthetic resin, mass production is facilitated. Therefore, the intraocular lens injection device 100 is provided as a disposable (throwaway) product.

In this embodiment, when a relative positional relation or an operation direction of each portion is described, as illustrated in FIG. 1, X1 direction is set as a tip side (front side), X2 direction is set as a rear end side (back side), Y1 direction is set as a left side (leftward), Y2 direction is set as a right side (rightward), Z1 direction is set as an upper side (upward), and Z2 direction is set as a lower side (downward). Among them, X1 direction and X2 direction correspond to an axial direction of the intraocular lens injection device 100, and Y1 direction and Y2 direction correspond to a width direction of the intraocular injection device 100, and Z1 direction and Z2 direction correspond to a height direction of the intraocular lens injection device 100.

Further, in this embodiment, the intraocular lens injection device 100 is supplied in a state of being housed (sealed) in a sterile bag. Then, a state in which the intraocular lens injection device 100 is housed in the sterile bag, or a state in which the intraocular lens injection device 100 is simply taken out from the sterile bag and no operation is applied thereto, is an initial state before use. FIG. 1 illustrates the initial state before use.

2. Configuration of the Intraocular Lens Injector

Figure 3:
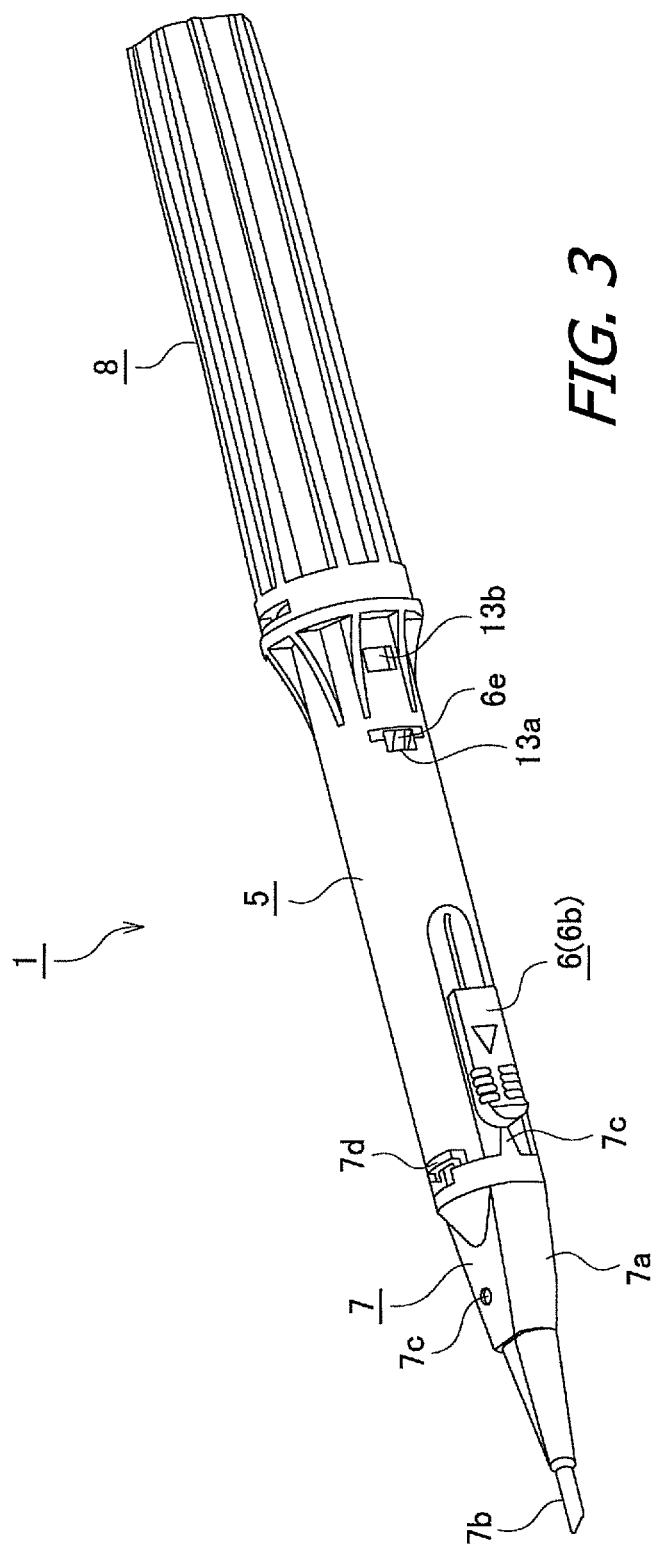
FIG. 3 is a perspective view illustrating the configuration of the intraocular lens injector.
Figure 4:
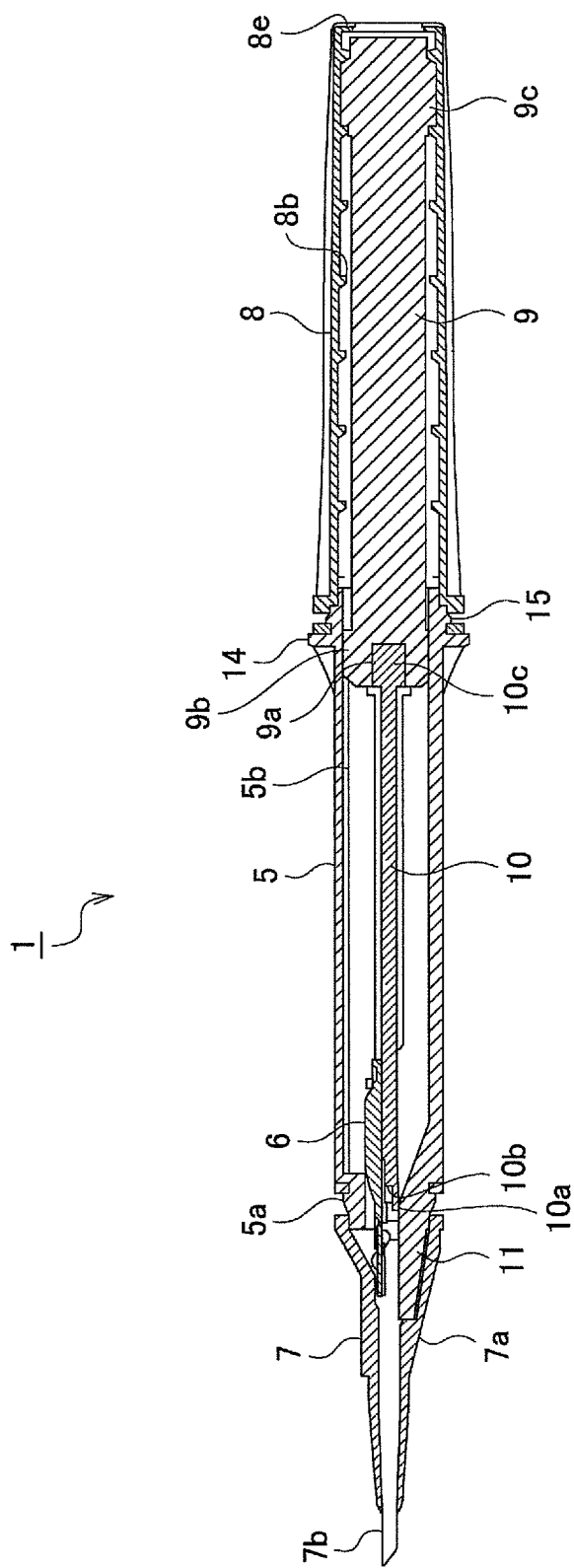
FIG. 4 is a cross-sectional view illustrating the configuration of the intraocular lens injector.

FIG. 3 is a perspective view illustrating a configuration of the intraocular lens injector, and FIG. 4 is a cross-sectional view illustrating the configuration of the intraocular lens injector.

The intraocular lens injector 1 is used in surgery to inject the intraocular lens into an eye. This embodiment handles an intraocular lens 4 as an example of the intraocular lens, which is made of a soft material such as silicone elastomer, etc., (see FIG. 6), having a circular optical portion 4a that functions optically, two support portions 4b that curve from two places on an outer circumferential part of the optical portion 4a so as to extend outwardly.

As illustrated in FIG. 2, the intraocular lens injector 1 is configured including an injector body 5, a slider 6, an injection tube 7, a screw member 8 as a rotating member, a plunger 9, and a rod 10. The slider 6 is mounted on the injector body 5. The injector body 5, the injection tube 7, and the screw member 8 are mutually connected to thereby configure a hollow body. Further, the plunger 9 and the rod 10 are mutually connected to thereby configure a moving member. In configuring the hollow body, the injection tube 7 is connected to the tip portion of the injector body 5, and the screw member 8 is connected to the rear end portion of the injector body 5. Further, in configuring the moving member, the rod 10 is connected to the tip portion of the plunger 9. The moving member including the plunger 9 and the rod 10, is housed in an interior of the hollow body composed of the injector body 5, the injection tube 7, and the screw member 8. Further detailed explanation will be give hereafter.

Injector Body

Figure 5:
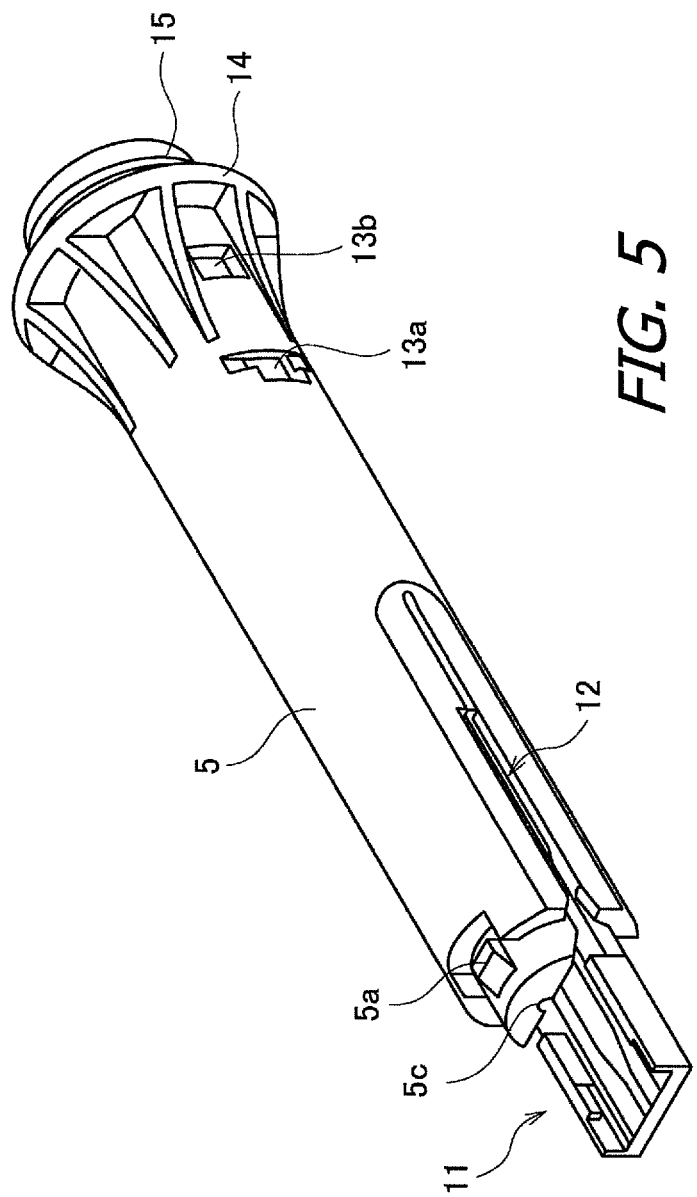
FIG. 5 is a perspective view illustrating the configuration of an injector body.

FIG. 5 is a perspective view illustrating the configuration of the injector body.

The injector body 5 is formed into a cylindrical shape as a whole. A lens placement portion 11 is provided on the tip portion of the injector body 5. The intraocular lens 4 is placed on the lens placement portion 11. The lens placement portion 11 is formed so as to protrude frontward from a lower side outer circumferential wall of the injector body 5. Further, an injection tube connecting portion 5a is formed on a tip side circumferential part of the injection body 5.

A slit 12, a pre-stage locking hole 13a, and a subsequent stage locking hole 13b are formed respectively on both sides of the injector body 5. The slit 12 is formed on the tip side of the injector body 5. The slit 12 movably (slidably) supports the slider 6 in a central axial direction of the injector body 5, when the slider 6 is mounted on the injector body 5. A recess groove 5b (see FIG. 4) is formed on an inner circumferential surface of the injector body 5. The recess groove 5b is formed in parallel to the axial direction of the injector body 5. The recess groove 5b is formed into a thin and long shape (elongated) over a full length of the injector body 5, excluding the lens placement portion 11 and the injection tube connecting portion 5a. Further, a slider engagement portion 5c is formed on the inner circumferential surface of the upper side injection connecting portion 5a. The slider engagement portion 5c functions to guide a movement of the slider 6, and is formed so as to be recessed into U-shape.

The pre-stage locking hole 13a and the subsequent stage locking hole 13b are formed on the rear end side of the injector body 5. The pre-stage locking hole 13a is an element of a reverse return prevention mechanism for preventing a reverse return of the slider 6 when the slider 6 is moved frontward in using the intraocular lens injector 1. Other element of the reverse return prevention mechanism will be described later. The reverse return of the slider 6 means a backward (in reverse direction) movement of the slider 6 after moving the slider 6 frontward. The subsequent stage locking hole 13b is formed on more rear end side of the injector body 5 than the pre-stage locking hole 13a. The subsequent stage locking hole 13b is the hole for positioning the slider 6 in the axial direction of the injector body 5. A flange 14 and a rotation support portion 15 are formed on the rear end portion of the injector body 5. The rotation support portion 15 is formed in a state of protruding backward of the flange 14. The rotation support portion 15 is formed into a cylindrical shape having a stepped configuration protruding into a ring shape. The rear end of the rotation support portion 15 is opened in a circular shape.

Figure 6:
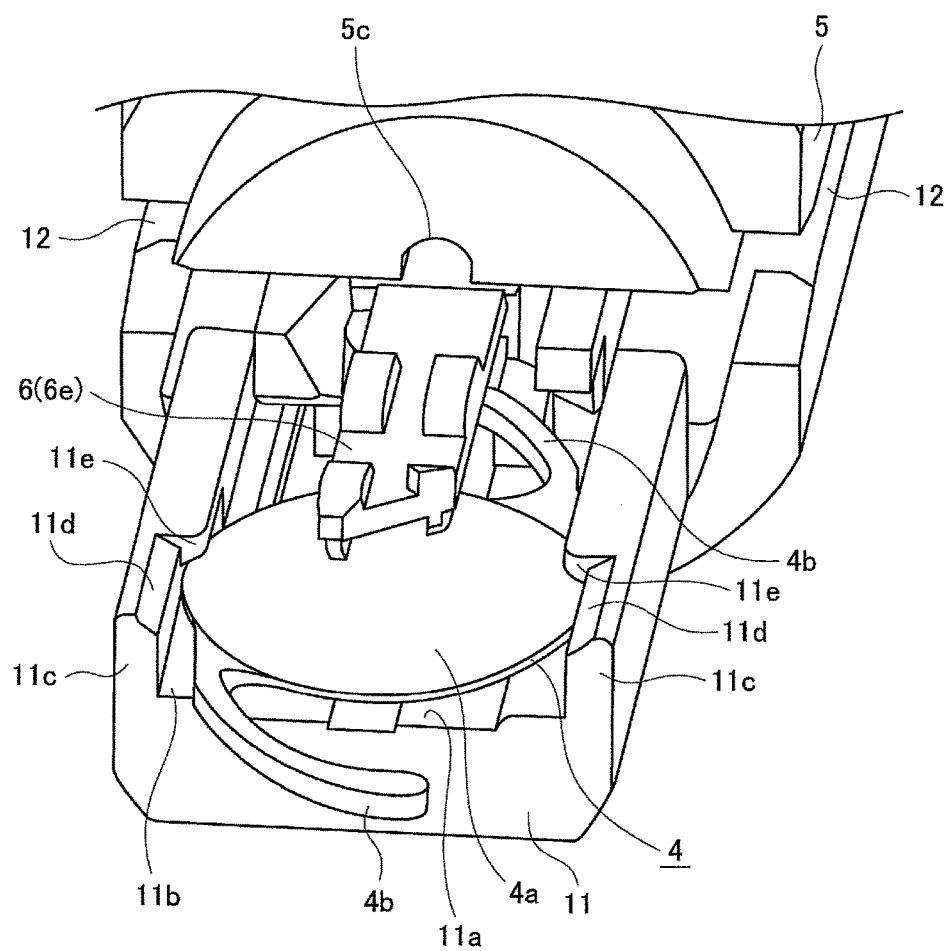
FIG. 6 is a perspective view expanding a tip portion of the injector body.
Figure 7:
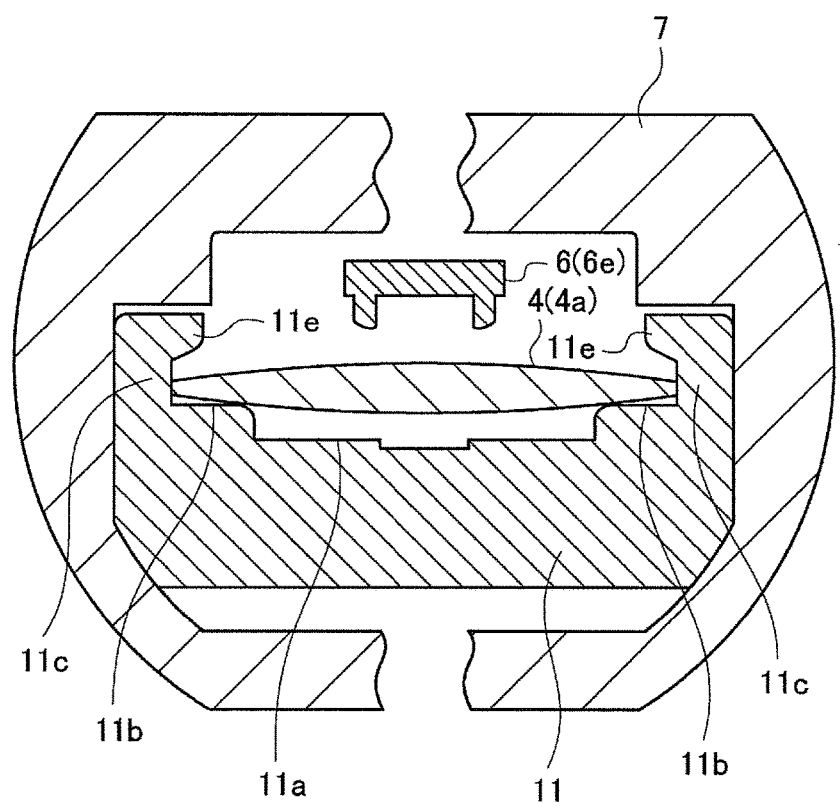
FIG. 7 is a cross-sectional view in the vicinity of a lens placement portion of the intraocular lens injector.

As illustrated in FIG. 6 and FIG. 7, the lens placement portion 11 includes a bottom surface portion 11a, lens receiving portions 11b, and lens guide portions 11c. The lens receiving portions 11b are configured to receive and support the intraocular lens 4 from below. The intraocular lens injector 1 is configured as a preload type in which the intraocular lens 4 is previously placed on the injector body 5. At this time, the intraocular lens 4 is placed in a state in which one of the support portions 4b is placed in front, and the other support portion 4b is placed in back.

A central part of the bottom surface portion 11a in a width direction, has a slightly recessed shape. The lens receiving portions 11b are formed on both right and left sides of the lens placement portion 11. The lens receiving portion 11b is formed so as to be one step higher than the bottom surface portion 11a. This is because when the intraocular lens 4 is supported by placing it on the lens receiving portion 11b, the intraocular lens 4 is supported in a state floating from the bottom surface portion 11a in not contact with the bottom surface portion 11a. Similarly to the lens receiving portions 11b, the lens guide portions 11c are formed on both right and left sides of the lens placement portion 11. The lens guide portions 11c are configured to guide the optical portion 4a of the intraocular lens 4 supported by the lens receiving portions 11b, so as to sandwich the optical portion 4a from both right and left sides. The lens guide portions 11c are formed in a vertically rise state from the lens receiving portions 11b. Inclined surfaces 11d and restricting portions 11e are formed on upper end portions of the right and left lens guide portions 11c so as to be adjacent to each other in the axial direction of the injector body 5. The inclined surfaces 11*d* are formed in an open-out shape so as to easily receive the intraocular lens 4 into the lens placement portion 11. The inclined surfaces 11*d* are formed on more tip side of the lens placement portion 11 than the restricting portions 11*e* in the axial direction of the injector body 5. The restricting portions 11*e* are configured to restrict a vertical movable range of the intraocular lens 4 supported by the lens receiving portion 11*b*.

Slider

Figure 8:
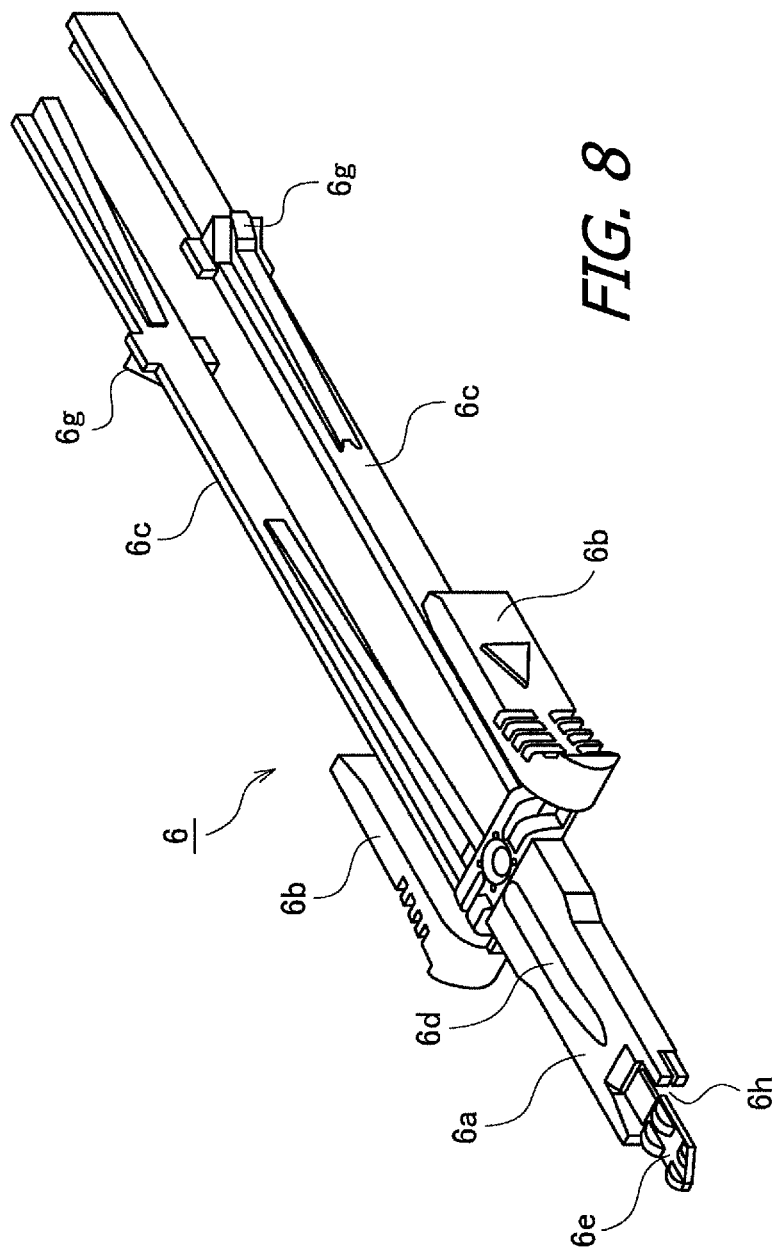
FIG. 8 is a perspective view illustrating a configuration of a slider.
Figure 9:
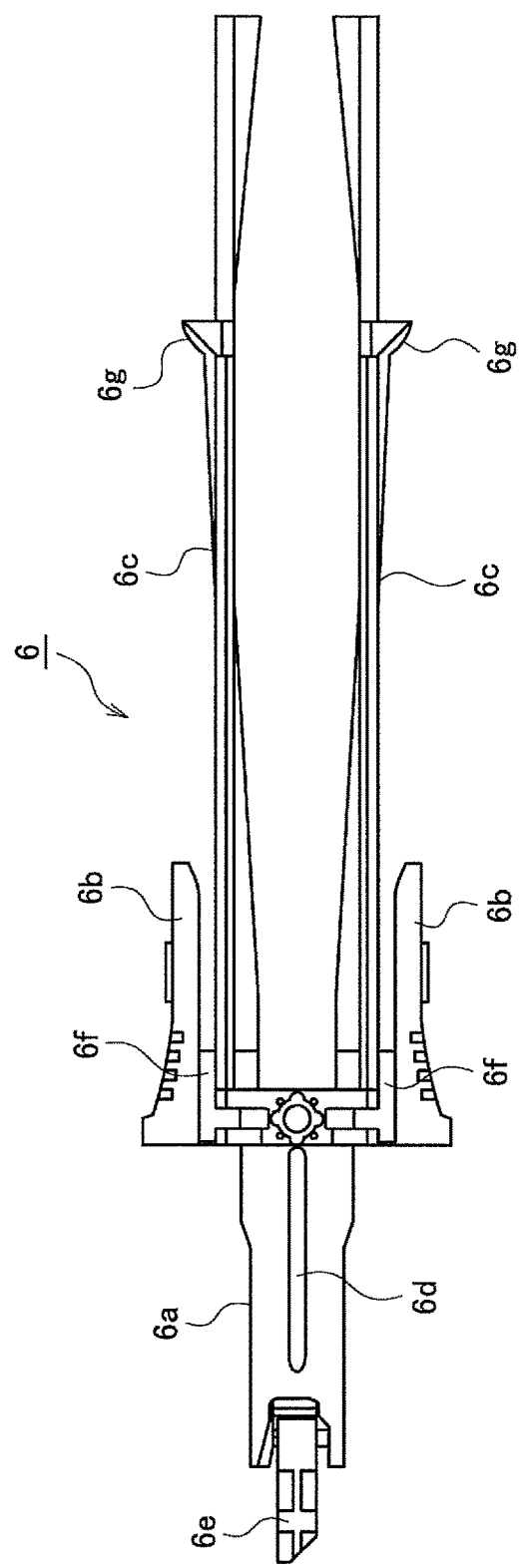
FIG. 9 is a plan view illustrating the configuration of the slider.

FIG. 8 is a perspective view illustrating the configuration of the slider, and FIG. 9 is a plan view illustrating the configuration of the slider.

The slider 6 is configured including a tip portion 6*a*, a pair of right and left wing portions 6*b*, and a pair of right and left leg portions 6*c*. The tip portion 6*a* is disposed on the tip portion of the slider 6. The tip portion 6*a* has a lens abutting portion 6*h*. The lens abutting portion 6*h* is a portion abutting on the intraocular lens 4 when the intraocular lens 4 is deformed into a prescribed shape by moving the slider 6. A guide rib 6*d* is formed on an upper surface of the tip portion 6*a*. The guide rib 6*d* is formed in the central part of the tip portion 6*a* in the width direction, in parallel to a longitudinal direction of the slider 6. The guide rib 6*d* is a portion engaging with the slider engagement portion 5*c* of the injector body 5. A lens pressing portion 6*e* is formed on the tip of the tip portion 6*a*. The lens pressing portion 6*e* extends frontward form the tip portion 6*a*. The lens pressing portion 6*e* is disposed in an upper part of the optical portion 4*a* of the intraocular lens 4 when the slider 6 is moved frontward (called a forward movement hereafter) from the initial state before use. A groove part (not illustrated) for guiding the movement of the rod 10, is formed on a lower surface of the tip portion 6*a*.

A pair of wing portions 6*b* is disposed outside of an outer wall portion of the injector body 5. A pair of wing portions 6*b* is the portions on which fingers (usually an index finger and thumb) of a user are added when the slider 6 is moved in the axial direction of the injector body 5 during use of the intraocular lens injector 1. The user refers to an operator such as an ophthalmologist who performs surgery, or a nurse who assists the operator. Irregularities for preventing slip or a mark indicating a moving direction of the slider 6 (triangular arrow in this embodiment) is formed on an outside surface of each wing portion 6*b*. Further, the outside surface of each wing portion 6*b* is curved toward the tip side from the rear end side so that the fingers of the user are easily caught, and the irregularities for preventing slip are formed on the curved portion. The wing portions 6*b* and the leg portions 6*c* are connected by shoulder portions 6*f*. Each shoulder portion 6*f* is a portion inserted (engaged) into/with the slit 12 of the injector body 5. The shoulder portion 6*f* is formed into a plate shape with a thickness corresponding to the width of the slit 12. Suitable gaps are formed between inner surfaces of the wing portions 6*b* and outer surfaces of the leg portions 6*c*.

A pair of leg portions 6*c* is disposed inside of the injector body 5, along the outer wall inner surface of the injector body 5. A stopper 6*g* is formed on each leg portion 6*c*. The stopper 6*g* is formed into a protruding shape on the outer surface of the leg portion 6*c*. The stopper 6*g* is formed corresponding to the abovementioned pre-stage locking hole 13*a* and the subsequent stage locking hole 13*b* of the injector body 5. The stopper 6*g* is other element of the abovementioned reverse return prevention mechanism.

Injection Tube

Figure 10:
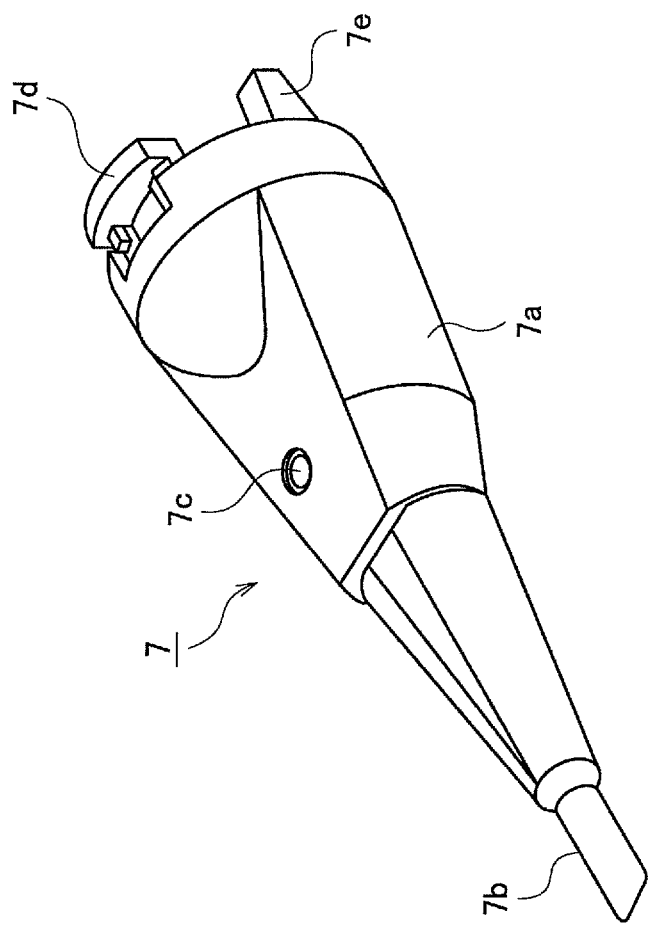
FIG. 10 is a perspective view illustrating the configuration of an injection tube.

FIG. 10 is a perspective view illustrating the configuration of the injection tube.

An injection tube 7 is configured to fold the intraocular lens 4 to be small and guide it into the eye, when the intraocular lens 4 is injected into the eye, the intraocular lens 4 being placed on the lens placement portion 11. The injection tube 7 includes a hollow injection tube body 7*a* and a thin tubular nozzle 7*b*. The injection tube 7 is mounted on the tip portion of the injector body 5. At this time, the lens placement portion 11 of the injector body 5 is disposed so as to be housed in the injection tube body 7*a* of the injection tube 7. A receiving hole 7*c* is formed on an upper surface of the injection tube body 7*a*. A hole (not illustrated) into which a tacking pin described later can be inserted, is formed on a lower surface of the injection tube body 7*a*. The rear end portion of the injection tube body 7*a* is opened, and a hook portion 7*d* and a wedge portion 7*e* are formed around the opening part. The hook portion 7*d* is a portion for hooking on the injection tube connecting portion 5*a* of the injector body 5, when the injection tube 7 is mounted on the tip portion of the injector body 5. The wedge portion 7*e* is a portion inserted into an entrance of the slit 12 of the injector body 5, when the injection tube 7 is mounted on the injector body 5. The tip side diameter of the injection tube body 7*a* becomes gradually smaller. The nozzle 7*b* is formed on the tip portion of the injection tube 7. The tip portion of the nozzle 7*b* is opened with an oblique cut. The tip portion of the nozzle 7*b* is a portion inserted into an incision of an eyeball, when the intraocular lens 4 is injected into the eye using the injector body 5.

Screw Member

Figure 11:
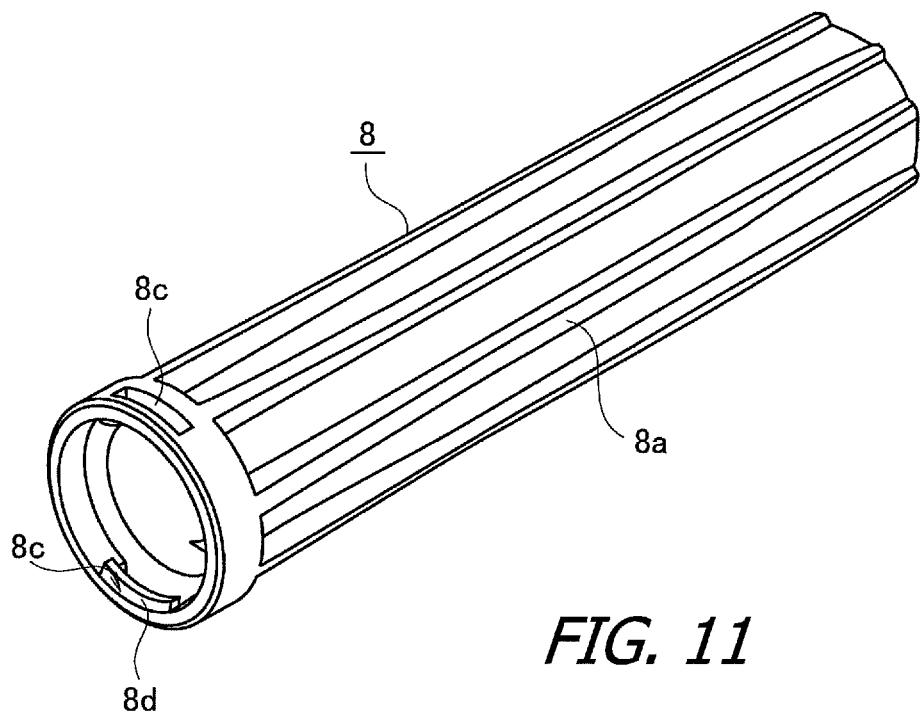
FIG. 11 is a perspective view illustrating the configuration of a screw member.
Figure 12:
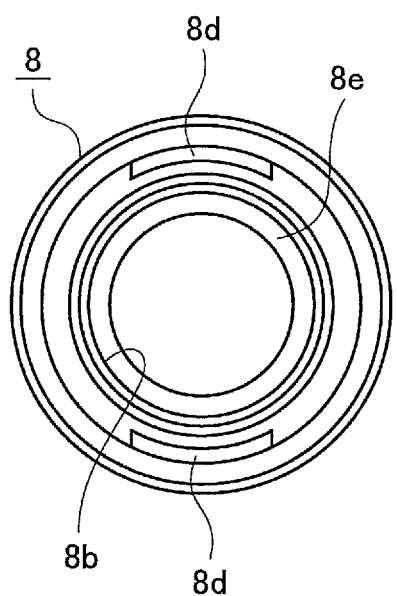
FIG. 12 is a front view illustrating the configuration of the screw member.

FIG. 11 is a perspective view illustrating the configuration of the screw member, and FIG. 12 is a front view illustrating the configuration of the screw member.

The screw member 8 is coaxially connected to the rear end portion of the injector body 5. In such a connection state, the screw member 8 is rotatably supported around the axis of the injector body 5. The screw member 8 is formed into a cylindrical shape. The tip portion and the rear end portion of the screw member 8 are opened in a circular shape respectively. A plurality of protrusions 8*a* are formed on the outer circumferential surface of the screw member 8. Each protrusion 8*a* is formed in parallel to the longitudinal direction of the screw member 8. Further, eight protrusions 8*a* in total are formed at an even angle pitch in a circumferential direction of the screw member 8. The screw member 8 is a portion which is rotary-operated by the user. At this time, when a plurality of protrusions 8*a* are formed on the outer circumferential surface of the screw member 8, the fingers of the user are caught on the protrusions 8*a*, and therefore the screw member 8 can be easily rotary-operated. As illustrated in FIG. 4, a first threaded portion 8*b* is formed on the inner circumferential surface of the screw member 8. The first threaded portion 8*b* constitutes a female screw. The first threaded portion 8*b* is formed substantially over an entire part of the axial direction of the screw member 8. Two window parts 8*c* are formed on the tip portion of the screw member 8. Two window parts 8*c* are formed at intervals of 180 degrees in the circumferential direction. The window parts 8*c* are configured to visually confirm whether the injector body 5 and the screw member 8 are properly connected. A pair of hook claws 8d is formed on the tip side inner circumferential part of the screw member 8. The hook claws 8d are formed on a tip side opening edge of the screw member 8 adjacent to the window part 8c. An abutting portion 8e is formed on the rear end portion of the screw member 8. The abutting portion 8e is formed by bending it inwardly so as to narrow an opening diameter of the rear end portion of the screw member 8. The abutting portion 8e is the portion on which the rear end portion of the plunger 9 is abutted, so that the plunger 9 is not protruded from the rear end portion of the screw member 8.

Plunger

Figure 13:
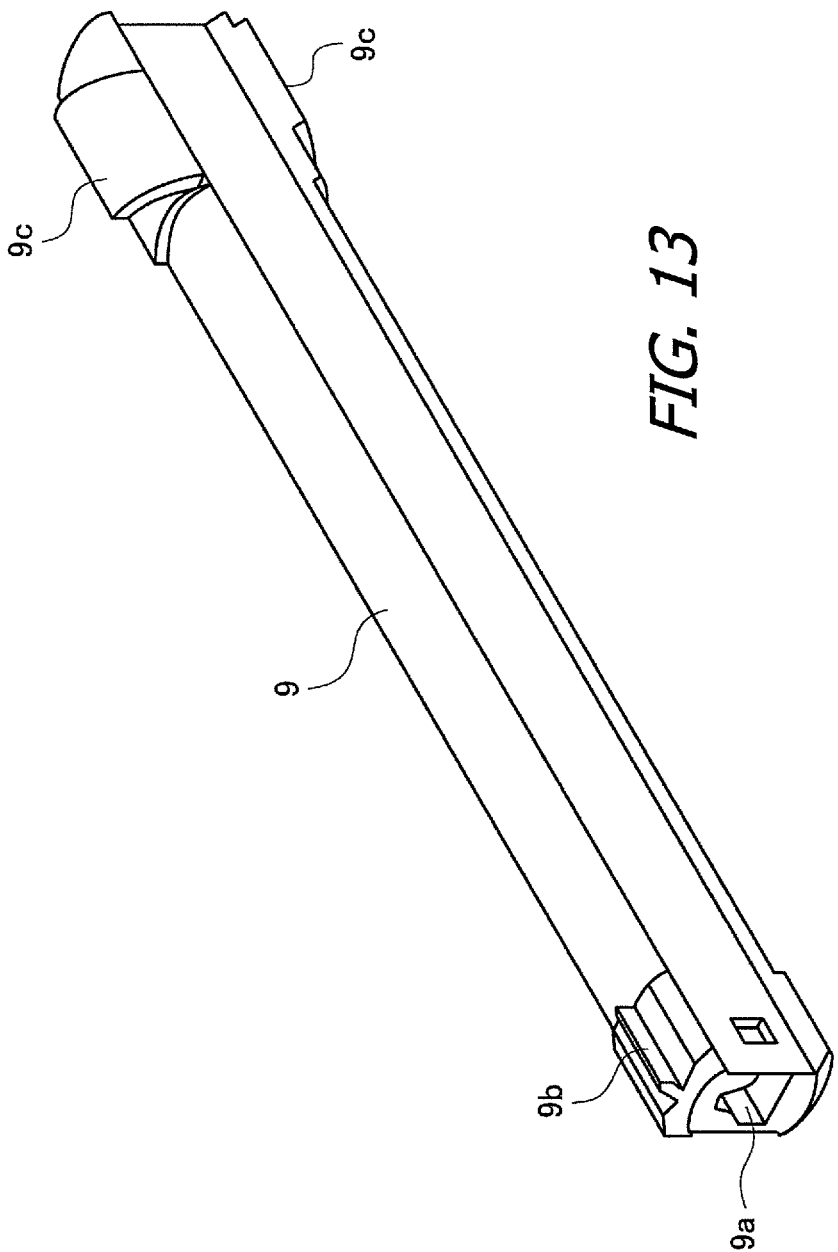
FIG. 13 is a perspective view illustrating the configuration of a plunger.

FIG. 13 is a perspective view illustrating the configuration of the plunger.

The plunger 9 is configured to move so that the injector body 5 and the screw member 8 move through the hollow part in the axial direction of the injector body 5. The plunger 9 is formed into a substantially prismatic shape. The plunger 9 is disposed in a state of being inserted into the screw member 8 so as not to be protruded from the rear end portion of the screw member 8, in the initial state before use. A connecting hole 9a is formed on a tip surface of the plunger 9. The connecting hole 9a is the hole for connecting the rod 10 to the tip portion of the plunger 9. A projection 9b is formed on the upper surface of the tip of the plunger 9, and corresponding thereto, a recessed groove 5b is formed on the inner circumferential surface of the injector body 5. The recessed groove 5b is configured to guide the plunger 9 movably in the axial direction of the injector body 5, by engaging with the projection 9b. A second threaded portion 9c is formed on the rear end portion of the plunger 9. The second threaded portion 9c constitutes a male screw, and is in a state always engaging with the first threaded portion 8b of the screw member 8. The second threaded portion 9c is formed as a pair formed in upper and lower parts of the plunger 9. When the intraocular lens injector 1 is used, the screw member 8 is operated to rotate around the axis of the injector body 5, thus moving the plunger 9 frontward. A movement starting position of the plunger at this time, is uniquely determined by abutting the rear end portion of the plunger 9 on ab abutting portion 8e of the screw member 8.

Rod

Figure 14:
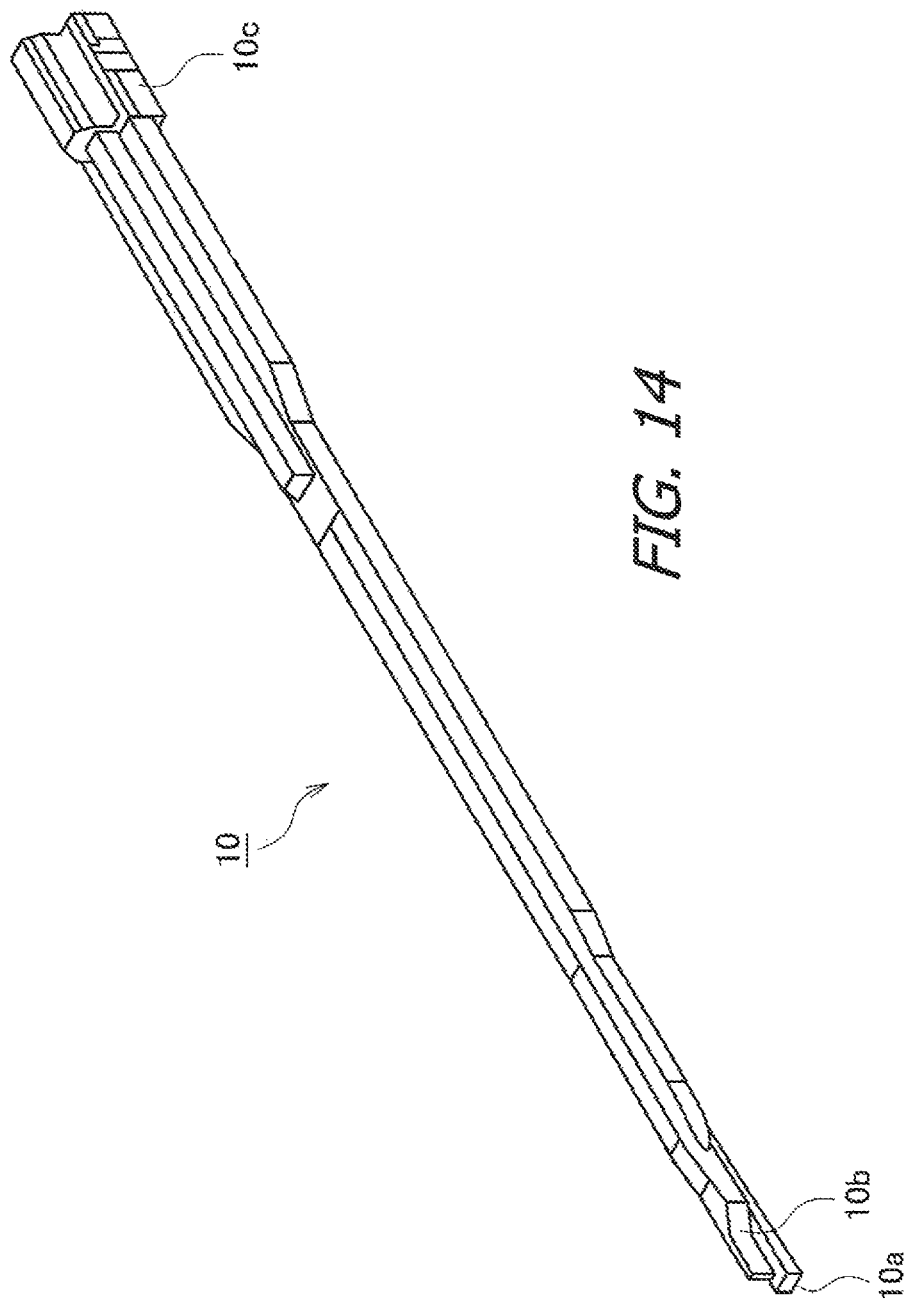
FIG. 14 is a perspective view illustrating the configuration of a rod.

FIG. 14 is a perspective view illustrating the configuration of the rod.

The rod 10 is configured to release the intraocular lens 4 placed on the lens placement portion 11, from an opening part of the nozzle 7b of the injection tube 7. The rod 10 is formed into an elongated (thin and long) shape. A first contact part 10a and a second contact part 10b are formed on the tip portion of the rod 10. When the intraocular lens 4 is pushed-out by the tip of the rod 10, the first contact part 10a is brought into contact with the optical portion 4a, and the second contact part 10b is brought into contact with the support portion 4b. An insertion portion 10c is formed on the rear end portion of the rod 10. The inserting portion 10c is the portion inserted into the connecting hole 9a of the plunger 9 when the rod 10 is connected to the plunger 9.

Case

The case 2 is configured including a front case 21 and a back case 22.

Front Case

Figure 15:
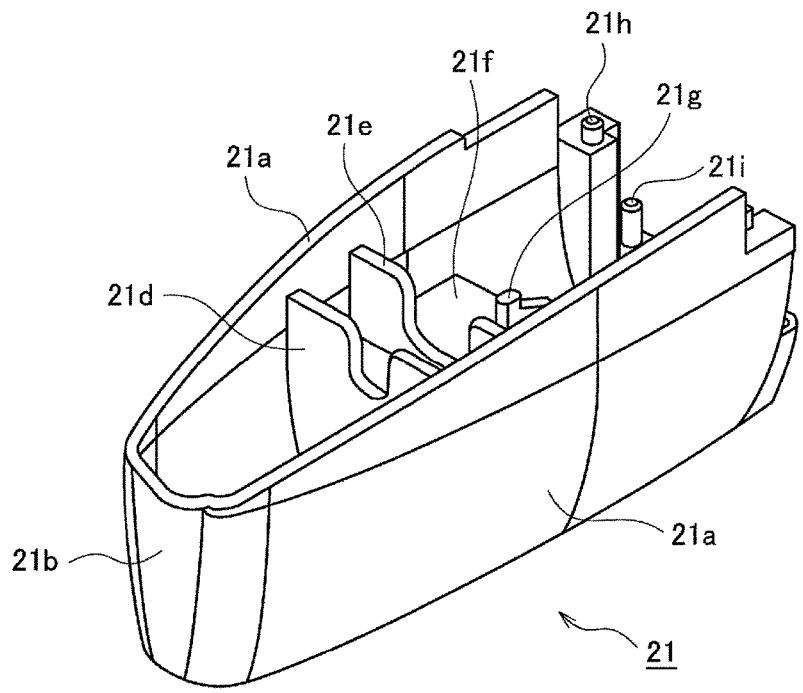
FIG. 15 is a perspective view illustrating the configuration of a front case.
Figure 16:
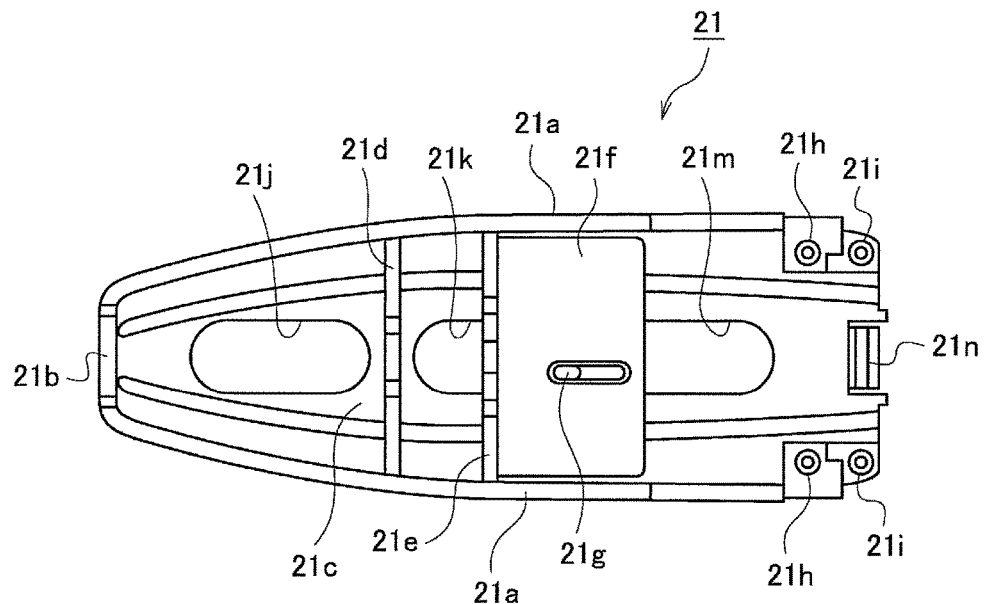
FIG. 16 is a plan view illustrating the configuration of the front case.

FIG. 15 is a perspective view illustrating the configuration of the front case, and FIG. 16 is a plan view illustrating the configuration of the front case.

The front case 21 has a pair of right and left side plates 21a, a front plate 21b, and a bottom plate 21c. Two receiving plates 21d and 21e are bridged over the right and left side plates 21a. An upper central part of each receiving plate 21d, 21e is notched into substantially U-shape respectively, so that the injection tube 7 is fitted and supported into/by the notched portion. A shelf part 21f is formed on a back side of the receiving plate 21e, and a tacking pin 21g is provided on the upper surface of the shelf part 21f. The tacking pin 21g is provided in a state of protruding upward. The rear end portion of the front case 21 is formed into stepped structure of upper and lower two stages. Then, a connecting pin 21h is provided on an upper stage, and a connecting pin 21i is provided on a lower stage. The connecting pins 21h and 21i are provided in right and left, one by one. Three holes 21j, 21k, and 21m, with positions shifted longitudinally, and a hook portion 21n are provided on the bottom plate 21c of the front case 21.

Back Case

Figure 17:
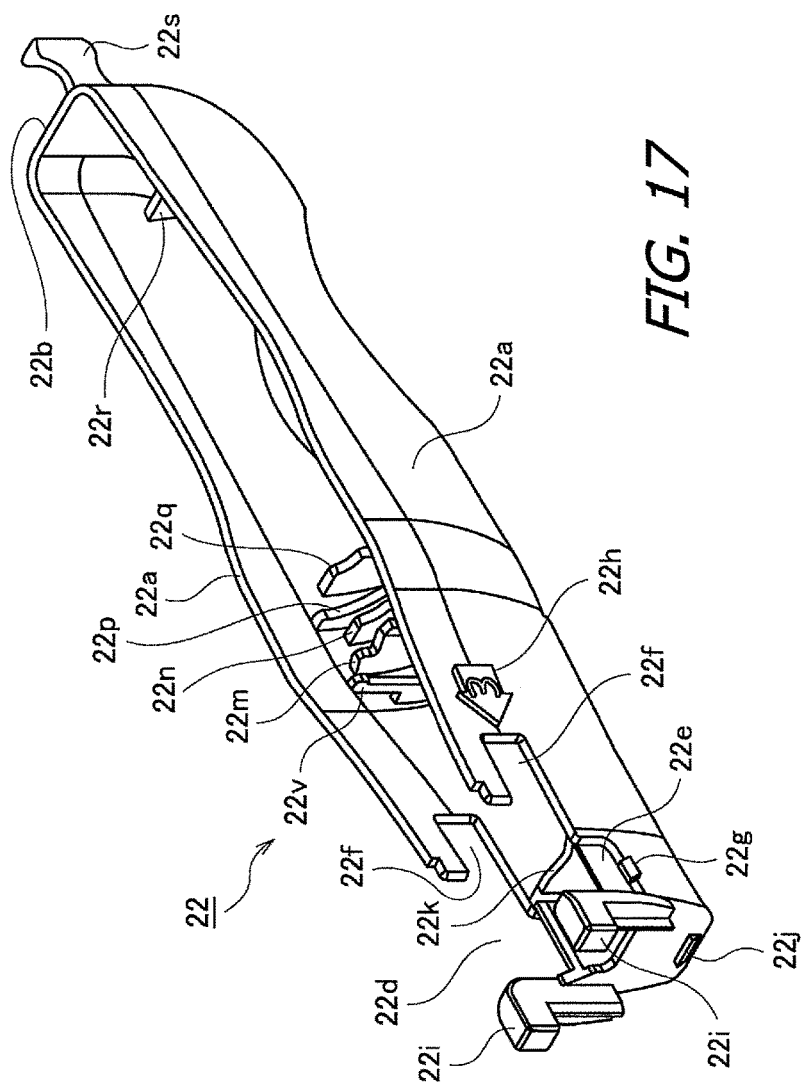
FIG. 17 is a perspective view illustrating the configuration of a back case.
Figure 18:
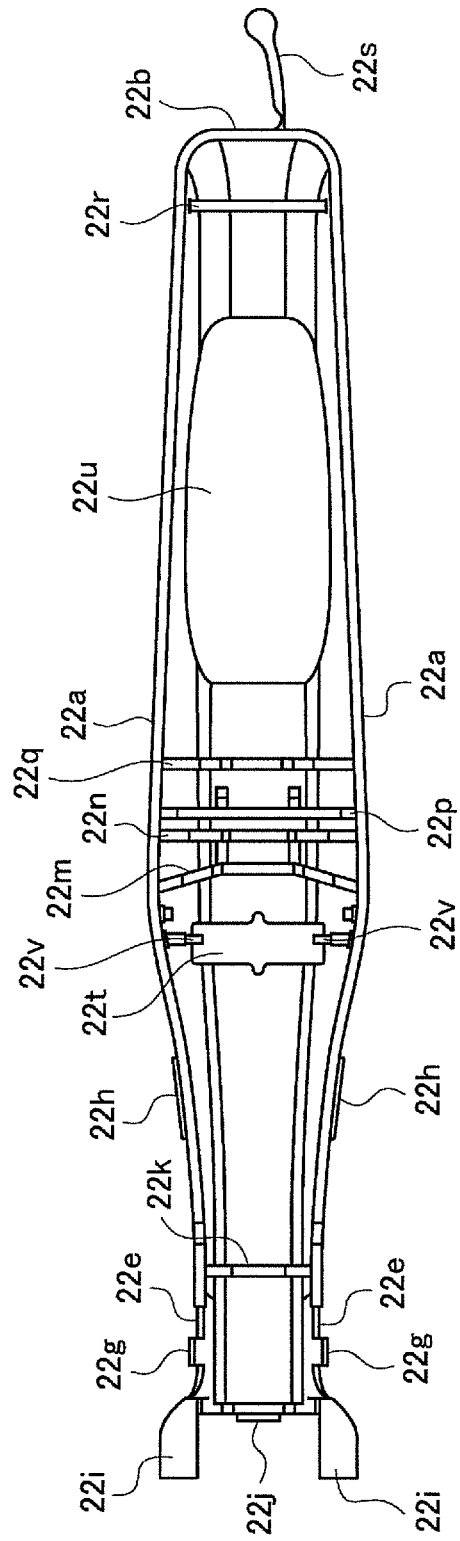
FIG. 18 is a plan view illustrating the configuration of the back case.

FIG. 17 is a perspective view illustrating the configuration of a back case, and FIG. 18 is a plan view illustrating the configuration of the back case.

The back case 22 has a pair of right and left side plates 22a, a back plate 22b, and a bottom plate 22c. On the right and left side plates 22a, a takeout recess portion 22d, a step portion 22e, and an engaging recess portion 22f are formed. The takeout recess portion 22d is formed so as to be notched downward from an upper side of the side plate 22a. The takeout recess portion 22d is formed so that a wing portion 6b of the slider 6 can be vertically retracted. The step portion 22e is the portion for mounting the case cover 3 on the case 2. The step portion 22e is also formed on the tip side lower part of the takeout recess portion 22d. The step portion 22e is formed so as to be slightly recessed inward of the side plate 22a. A protrusion 22g is formed on a lower end portion of the step portion 22e. The engaging recess portion 22f is formed in communication with the takeout recess portion 22d. The engaging recess portion 22f is formed by extending a part of the side plate 22a frontward. An arrow 22h enclosing the number "3" for indicating an operation procedure when using the intraocular lens injector 1, is formed in the vicinity of the engaging recess portion 22f. The arrow 22h indicates an operation direction for moving the slider 6 in the axial direction of the injector body 5. The arrow 22h is formed on an outside surface of each side plate 22a, integrally with the side plate 22a by resin molding.

A pair of right and left connecting portions 22i is formed on the tip portion of the back case 22. When the intraocular lens injector 1 is housed in the case 2, the right and left connecting portions 22i guides the intraocular lens injector 1 to a prescribed housing position by sandwiching a connecting portion of the injector body 5 and the injection tube 7 from both sides. Each connecting portion 22i has a stepped structure corresponding to arrangements of connecting pins 21h and 21i of the front case 21. A communicating hole (not illustrated) that can be engaged with the connecting pin 21i is formed on an upper stage side of the connecting portion 21i, and a communicating hole (not illustrated) that can be engaged with the connecting pin 21i is formed on a lower stage side of the connecting portion 21i. Further, a claw 22j is formed on the tip portion of the back case 22. When the front case 21 and the back case 22 are connected, the claw 22j is the portion on which a hook portion 21n of the front case 21 is hooked. Six receiving plates 22k, 22m, 22n, 22p, 22q, and 22r in total are bridged over the right and left side plates 22a. Among them, the receiving plates 22k, 22m, and 22n are the plates for receiving and supporting the injector body 5 from under, and the receiving plates 22p and 22q are the plates for supporting the screw member 8 from under, when the intraocular lens injector 1 is housed in the case 2. When the intraocular lens injector 1 is taken-out from the case 2, the receiving plate 22r is the plate for receiving and supporting the rear end portion of the screw member 8 from under.

A handle 22s is formed on a back plate 22b. The handle 22s is the portion gripped by a user, when the user takes out the intraocular lens injection device 100 from a sterile bag.

Two holes 22t and 22u are formed on the bottom plate 22c, with positions shifted in a back-and-forth direction. The hole 22t is formed between the receiving plate 22k and the receiving plate 22m in a longitudinal direction of the back case 22, and the hole 22u is formed between the receiving plate 22q and the receiving plate 22r. The hole 22t is a long hole in which a width direction of the back case 22 is a long axial direction. Guide pieces 22v are formed on an inner surface of the right and left side plates 22a respectively corresponding to the positions of the holes 22t. When the intraocular lens injector 1 is housed in the case 2, the right and left guide pieces 22v are the pieces for guiding the intraocular lens injector 1 to a prescribed position by sandwiching the injector body 5 from both sides. On a formation site of the hole 22u, the right and left side plates 22a are notched into an arc shape in a side view.

The front case 21 and the back case 22 having the abovementioned configurations, are connected as follows. Namely, two connecting pins 21h and 21i formed on stepped structures on the rear end portion of the front case 21, are fitted into two holes (not illustrated) formed on the stepped structure of the connecting portion 22i of the back case 22. Also, the hook portion 21n formed on the rear end portion of the front case 21 is locked on the claw 22j formed on the tip portion of the back case 22 corresponding to the hook portion 21n. Thus, the case 2 is constituted.

Case Cover

Figure 19:
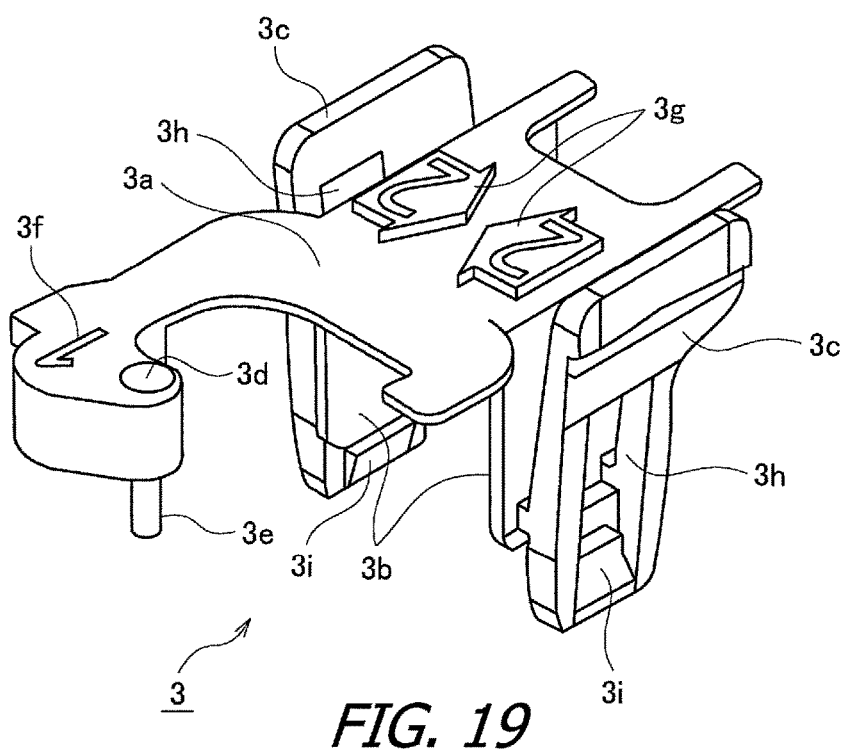
FIG. 19 is a perspective view illustrating the configuration of a case cover.

FIG. 19 is a perspective view illustrating the configuration of the case cover.

The case cover 3 has a plate-shaped cover body 3a, a pair of right and left holding pieces 3b, and a pair of right and left movable pieces 3c.

An injection port 3d is formed on the tip portion of the cover body 3a. The injection port 3d is the port for injecting a viscoelastic substance (such as hyaluronate sodium). An upper part of the injection port 3d is opened into a bowl shape. A pipe 3e is formed just under the injection port 3d. The pipe 3e is protruded downward coaxially with the injection port 3d. The pipe 3e has a hole continued to the pipe 3e. The pipe 3e is the pipe for releasing the viscoelastic substance which is injected from the injection port 3d, to the vicinity of the intraocular lens 4 placed on the lens placement portion 11 of the injector body 5, by being inserted into the receiving hole 7c of the injection tube 7. Mark "3f" of numeral "1" is engraved in the vicinity of the injection port 3d, for indicating the operation procedure when using the intraocular lens injector 1. The engraved mark "3f" is integrally formed on the upper surface of the cover body 3a by resin molding. Also, a pair of right and left arrows 3g are formed, enclosing numeral "2" that indicates the operation procedure when using the intraocular lens injector 1. The arrows 3g indicate the operation direction when operating right and left movable pieces 3c so as to sandwich them by fingers.

A pair of clamping pieces 3b is formed to hang down from right and left both sides of the cover body 3a. Each side view shape of the clamping pieces 3b, is formed corresponding to the side view shapes of the takeout recess portion 22d and the step portion 22e of the front case 21.

A pair of movable pieces 3c is provided on right and left both sides of the cover body 3a. The movable pieces 3c are connected to the clamping pieces 3b in the vicinity of the lower edges of the clamping pieces 3b. The movable pieces 3c are disposed slightly inclined with respect to the clamping pieces 3b, so that a V-shaped gap is formed between the clamping pieces 3b and the movable pieces 3c. Each movable piece 3c is formed to be thicker than each clamping piece 3b. Drain holes 3h and locking members 3i are formed on the movable pieces 3c. Each drain hole 3h is formed in a long rectangular shape in a vertical direction. The locking member 3i is formed on the lower end portion of each movable piece 3c. When the case cover 3 is mounted on the case 2, the locking member 3i is the portion where the protrusion 22g of the back case 22 is locked.

<3. Assembly Method of the Intraocular Lens Injection Device>

An assembly method of the intraocular lens injection device 100 will be described next.

Figure 20:
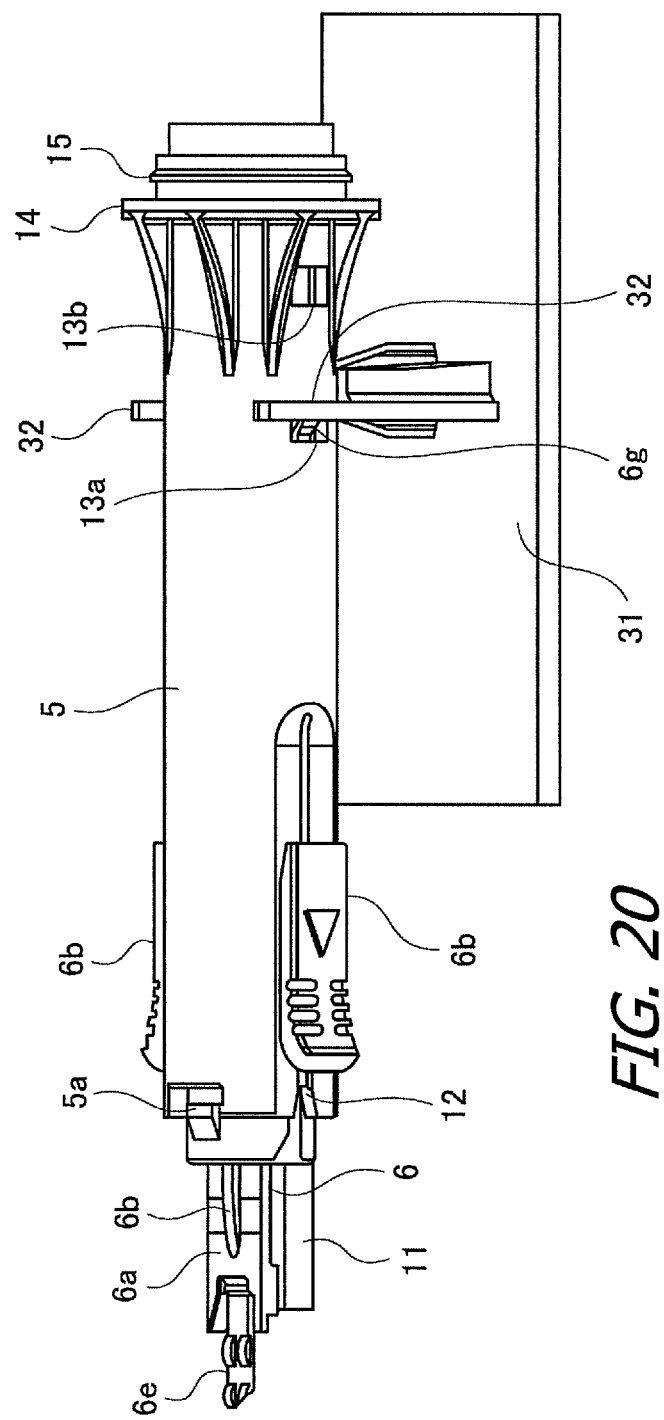
FIG. 20 is a perspective view illustrating a state in which an injector body is set in an assembly jig.

First, the slider 6 is attached to the injector body 5. At this time, the leg portion 6c of the slider 6 is inserted from a tip side opening part of the injector body 5. Further, the shoulder portion 6f of the slider 6 is inserted and engaged into/with the slit 12 of the injector body 5, and the slider 6 is pushed-in backward in this state. When the slider 6 is thus pushed-in, the stopper 6g of the slider 6 is caught in the pre-stage locking hole 13a of the injector body 5, and the slider 6 cannot be pushed-in any more. Therefore, when the slider 6 is attached to the injector body 5, an assembly jig 31 illustrated in FIG. 20 is used. The assembly jig 31 has a pair of release levers 32. The pair of release levers is the lever for preventing the stopper 6g from being caught in the pre-stage locking hole 13a. When the injector body 5 is set on the assembly jig 31, the slider 6 is pushed-in backward until the stopper 6g passes through the pre-stage locking hole 13a and is caught in the subsequent stage locking hole 13b. At this time, the guide rib 6d of the slider 6 is engaged with the slider engagement portion 5c of the injector body 5.

On the other hand, the plunger 9 is attached to the screw member 8. Specifically, the screw member 8 is fitted into the rear end portion of the plunger 9 so as to cover the tip side opening of the screw member 8, to thereby rotate the screw member 8. Thus, the first threaded portion 8b and the second threaded portion 9c are engaged with each other. Therefore, when the plunger 9 is fixed and the screw member 8 is rotated, the plunger 9 is inserted into the screw member 8, with a rotation of the screw member 8. At this time, the screw member 8 is rotated until the rear end portion of the plunger 9 abuts on the abutting portion 8e of the screw member 8. Thus, the rear end portion of the plunger 9 is disposed at a position slightly retracted inward of the rear end portion of the screw member 8. Further, the tip portion of the plunger 9 is disposed in a state of protruding slightly frontward of the tip portion of the screw member 8. Next, the rod 10 is attached to the plunger 9. Specifically, the inserting portion 10c of the rod 10 is inserted into the connecting hole 9a of the plunger 9. Thus, the connecting hole 9a and the inserting portion 10c are caught in each other, and the rod 10 cannot be slipped-off from the plunger 9.

Figure 21:
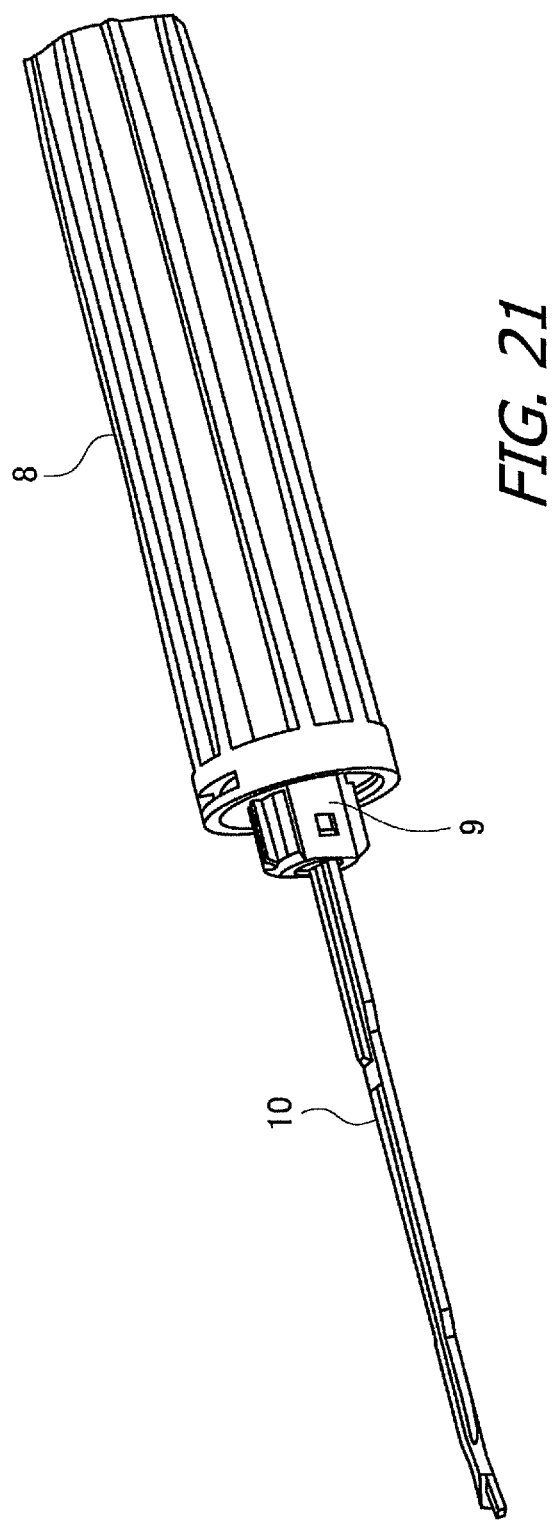
FIG. 21 is a perspective view illustrating an assembly composed of the screw member, the plunger, and the rod.

Thus, as illustrated in FIG. 21, an assembly composed of the screw member 8, the plunger 9, and the rod 10 is obtained.

Next, the tip portion of the screw member 8 is connected to the rear end portion of the injector body 5. At this time, the rod 10 is inserted into the injector body 5 from backward. The tip side of the rod 10 is passed through the bottom of the tip portion 6a of the slider 6. Further, the projection 9b of the plunger 9 is engaged with the recess groove 5b of the injector body 5, and in this state, the screw member 8 is connected to the injector body 5. At this time, the screw member 8 is slightly strongly pushed-in to the injector body 5, so that the hook claw 8d of the screw member 8 can overcome a ledge portion of the rotation support portion 15. Thus, the screw member 8 is freely rotatably connected to the rear end portion of the injector body 5.

Next, the injector body 5 and the screw member 8 connected to each other as described above, are housed in the back case 22. At this time, the slider 6 is moved frontward before the injector body 5 and the screw member 8 are housed in the back case 22. This is because the wing portion 6b of the slider 6 is caught by the side plate 22a of the back case 22 in a state when the slider 6 is moved backward. When the slider 6 is moved frontward, the stopper 6g is caught in the pre-stage locking hole 13a of the injector body 5, thus preventing the slider 6 from returning backward. Therefore, the abovementioned assembly jig 31 is set in the back case 22. At this time, the release lever 32 of the assembly jig 31 is disposed in the back case 22 through the hole 22t of the back case 22. After the injector body 5 and the screw member 8 are housed in the back case 22 in this state, the slider 6 is pushed backward until the stopper 6g is caught in the subsequent stage locking hole 13b. At this time, the stopper 6g of the slider 6 passes through the pre-stage locking hole 13a of the injector body 5 and is fitted into the subsequent stage locking hole 13b. Thus, the slider 6 is positioned at a prescribed position in the axial direction of the injector body 5. Thereafter, the assembly jig 31 is removed from back case 22.

Next, as illustrated in FIG. 6, the intraocular lens 4 is placed on the lens placement portion 11 of the injector body 5. At this time, the optical portion 4a of the intraocular lens 4 is placed on the lens receiving portion 11b. Further, one of the support portions 4b of the intraocular lens 4 is disposed in front, and the other support portion 4b is disposed in the back.

Next, the injection tube 7 is attached to the tip portion of the injector body 5. At this time, the hook portion 7d of the injection tube 7 is hooked on the injection tube connecting portion 5a of the injector body 5 to be engaged. Further, the wedge portion 7e of the injection tube 7 is inserted into the slit 12 of the injector body 5.

Next, the case cover 3 is attached to the back case 22. At this time, the case cover 3 is disposed to cover the back case 22 from above, while the clamping piece 3b of the case cover 3 is positioned at the step portion 22e of the back case 22. Then, the protrusion 22g of the back case 22 is caught by the locking member 3i of the movable piece 3c to be locked. Further, the pipe 3e of the case cover 3 is inserted into the receiving hole 7c of the injection tube 7.

Next, the front case 21 is attached to the back case 22. At this time, the tacking pin 21g of the front case 21 is inserted into the hole (not illustrated) provided on a lower surface of the injection tube 7. The tacking pin 21g is disposed slightly frontward of the intraocular lens 4 which is placed on the lens placement portion 11.

As described above, the assembly of the intraocular lens injector 1 incorporating the intraocular lens 4, and the assembly of the intraocular lens injection device 100 in a state that the intraocular lens injector 1 is housed in the case 2 and the case cover 3 is mounted thereon, are completed. The intraocular lens injection device 100 whose assembly is completed, is housed in a sterile bag not illustrated.

4. Method of Using the Intraocular Lens Injection Device

A method of using the intraocular lens injection device 100 will be described next.

The intraocular lens injection device 100 is supplied to a user in a state of being housed in the sterile bag not illustrated. Therefore, the user opens the sterile bag and takes out the intraocular lens injection device 100 from the sterile bag while holding a handle 22s.

Thereafter, the user operates the intraocular lens injection device 100 in accordance with the operation procedure indicated by the engraved mark 3f or arrow 3g of the case cover 3, and arrow 22h of the case 2. In this case, the engraved mark 3f indicates "1" as the operation procedure, and arrow 3g indicates "2" as the operation procedure, and arrow 22h indicates "3" as the operation procedure. Therefore, the user performs the following work in an order of the operation procedure "1"→"2"→"3".

Operation Procedure "1"

First, the user injects the viscoelastic substance into the injection port 3d of the case cover 3 in accordance with the operation procedure indicated by the engraved mark 3f of the case cover 3. The injected viscoelastic substance is supplied to the intraocular lens 4 from the injection port 3d through the pipe 3e.

Operation Procedure "2"

Next, the user removes the case cover 3 from the case 2. At this time, the user sandwiches the upper part of the pair of movable pieces 3c from right and left both sides in accordance with the operation procedure and the operation direction indicated by the arrow 3g of the case cover 3. Then, the lower part of each movable piece 3c is displaced to outside, and accordingly the lower part of the clamping piece 3b is also displaced to outside. Thus, a lock state of the protrusion 22g of the injector body 5 and the locking member 3i of the case cover 3 is canceled. Therefore, by pulling-up the case cover 3, with a pair of movable pieces 3c sandwiched from both sides, the user removes the case cover 3 from the case 2. In this stage, the wing portion 6b of the slider 6 is engaged with the engaging recess portion 22f, thus preventing the takeout of the intraocular lens injector 1 from the case 2.

Operation Procedure "3"

Figure 22:
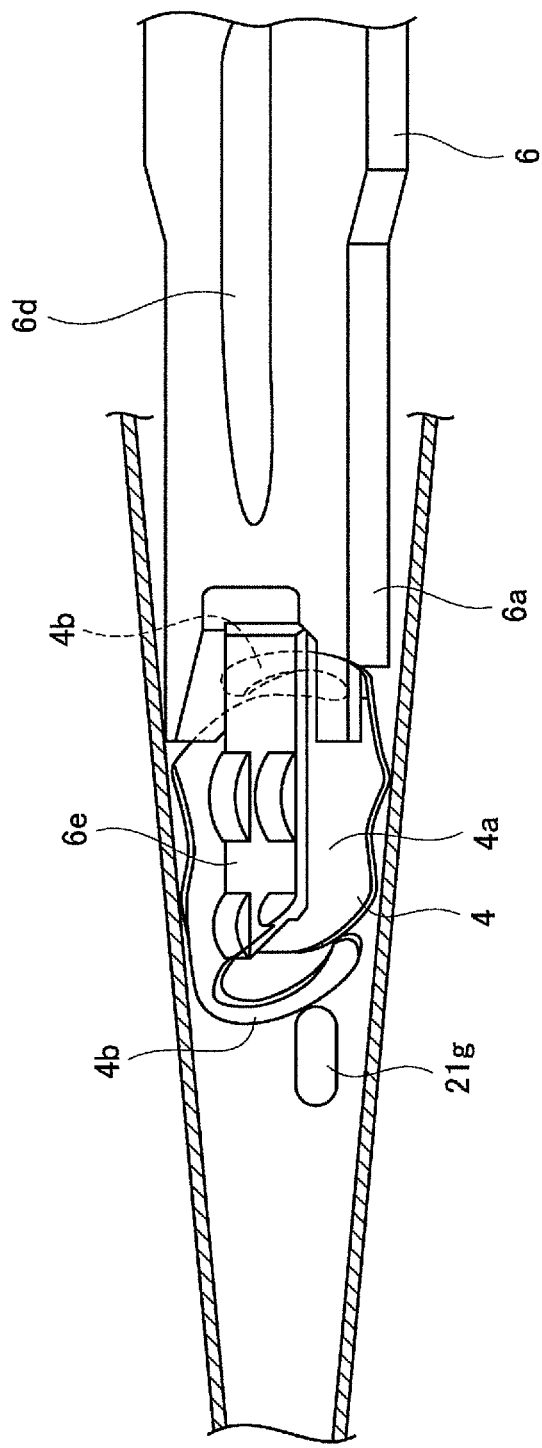
FIG. 22 is a view illustrating a state of the intraocular lens when the slider is moved forward.

Next, the user moves the slider 6 frontward. At this time, the user moves the slider 6 frontward in accordance with the operation procedure and the operation direction indicated by the arrow 22h of the injector body 5. Thus, the wing portion 6b of the slider 6 moves to the takeout recess portion 22d from the engaging recess portion 22f. Therefore, a state of preventing the takeout of the intraocular lens injector 1 (called a takeout prevention state), is canceled. Further, the stopper 6g of the leg portion 6c is separated from the subsequent stage locking hole 13b of the injector body 5 due to advancement of the slider 6, and fitted into the pre-stage locking hole 13a. Accordingly, reverse return of the slider 6 is prevented. On the other hand, the lens abutting portion 6h of the slider 6 abuts on the intraocular lens 4 due to the movement of the slider 6, thus pushing out the intraocular lens 4 in this stated. Thus, the intraocular lens 4 is deformed into a prescribed shape. Specifically, as illustrated in FIG. 22, the support portion 4b disposed in front is pushed against the tacking pin 21g of the front case 21 and folded back toward the optical portion 4a, and the support portion 4b disposed in back is pushed against the lens abutting portion 6g and folded back toward the optical portion 4a.

When performing the work in accordance with the operation procedure "1"→"2"→"3", the user takes out the intraocular lens injector 1 from the case 2. In this stage, the wing portion 6b advances to a point of the takeout recess portion 22d due to the abovementioned movement of the slider 6, thus canceling the takeout prevention state, and therefore the intraocular lens injector 1 is taken out from the case 2.

Next, by operating the intraocular lens injector 1, the user releases the intraocular lens 4 from the tip of the injection tube 7. At this time, by releasing the intraocular lens 4 in a state of inserting the tip portion of the injection tube 7 into the incision of the eyeball, the intraocular lens 4 is inserted into the eye. Further, the shape of the intraocular lens 4 after inserting into the eye, is restored to its original shape.

The operation of the intraocular lens injector 1 is performed by rotating the screw member 8 in one direction (referred to as a "positive rotation" hereafter). At this time, the first threaded portion 8b of the screw member 8 and the second threaded portion 9c of the plunger 9 are always engaged with each other, including an initial state before use. Therefore, at the time of the positive rotation of the screw member 8, simultaneously with this rotation, the plunger 9 starts to move toward the injector body 5 (frontward). Further, at the time of the rotation of the screw member 8 in a reverse direction by the user accidentally in the initial state before use, the rear end portion of the plunger 9 abuts on the abutting portion 8e of the screw member 8. Therefore, the reverse rotation (misoperation) of the screw member 8 is prevented. That is, the abutting portion 8e of the screw member 8 and the rear end portion of the plunger 9 that abuts on the abutting portion 8e, constitute a reverse rotation prevention mechanism of preventing the reverse rotation of the screw member 8 in the initial state before use.

The positive rotation of the screw member 8 refers to the rotation of the screw member 8 when the plunger 9 moves frontward by the engagement of the threaded portions when the screw member 8 is rotated. Further, the reverse rotation of the screw member 8 refers to the rotation of the screw member 8 when the plunger 9 is moved backward by the engagement of the threaded portions when the screw member 8 is rotated.

When the screw member 8 is rotated as described above, the plunger 9 and the rod 10 are moved frontward, according to the number of rotations. Outer wall portions of the injector body 5, the injection tube 7, and the screw member 8 are respectively semitransparent. Therefore, the user can visually confirm the movement of the plunger 9 and the rod 10 by looking it through the outer wall portions of the injector body 5, the injection tube 7, and the screw member 8.

Figure 23:
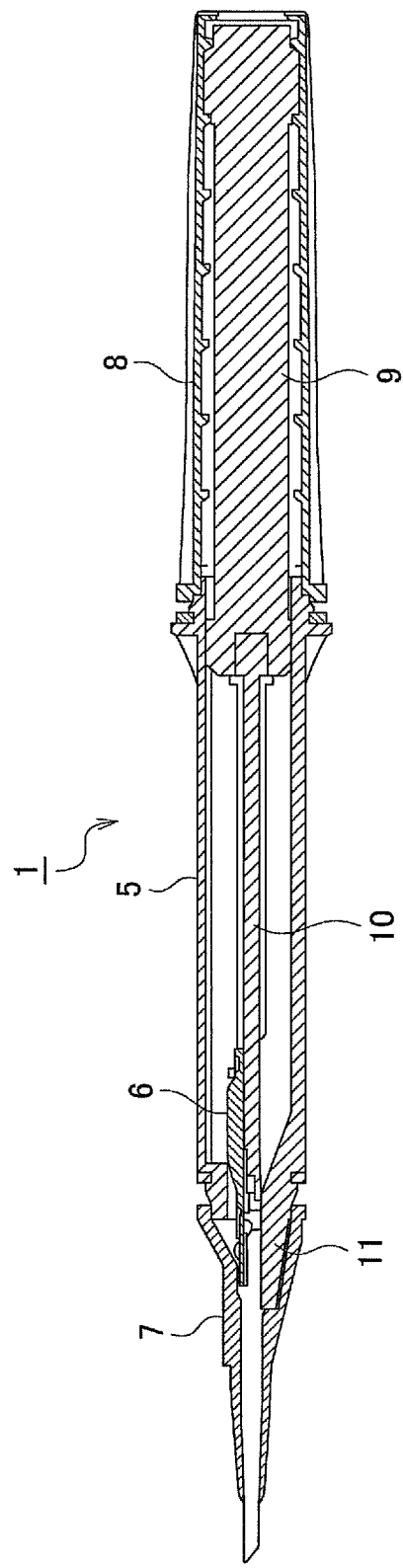
FIG. 23 is a cross-sectional view illustrating a positional relation of each portion before the slider is moved forward.
Figure 24:
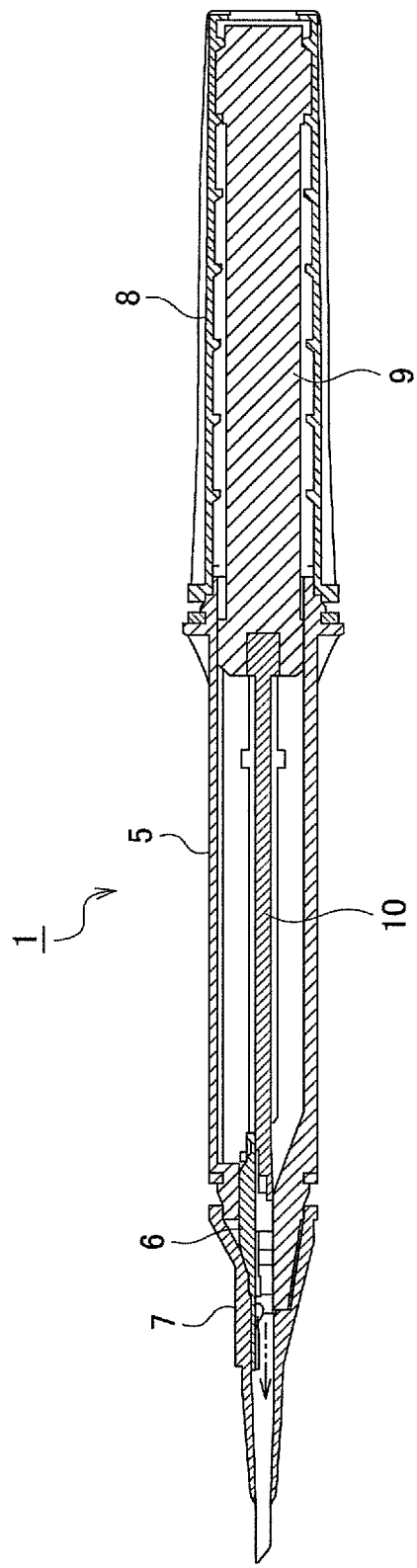
FIG. 24 is a cross-sectional view illustrating the positional relation of each portion after the slider is moved frontward.
Figure 25:
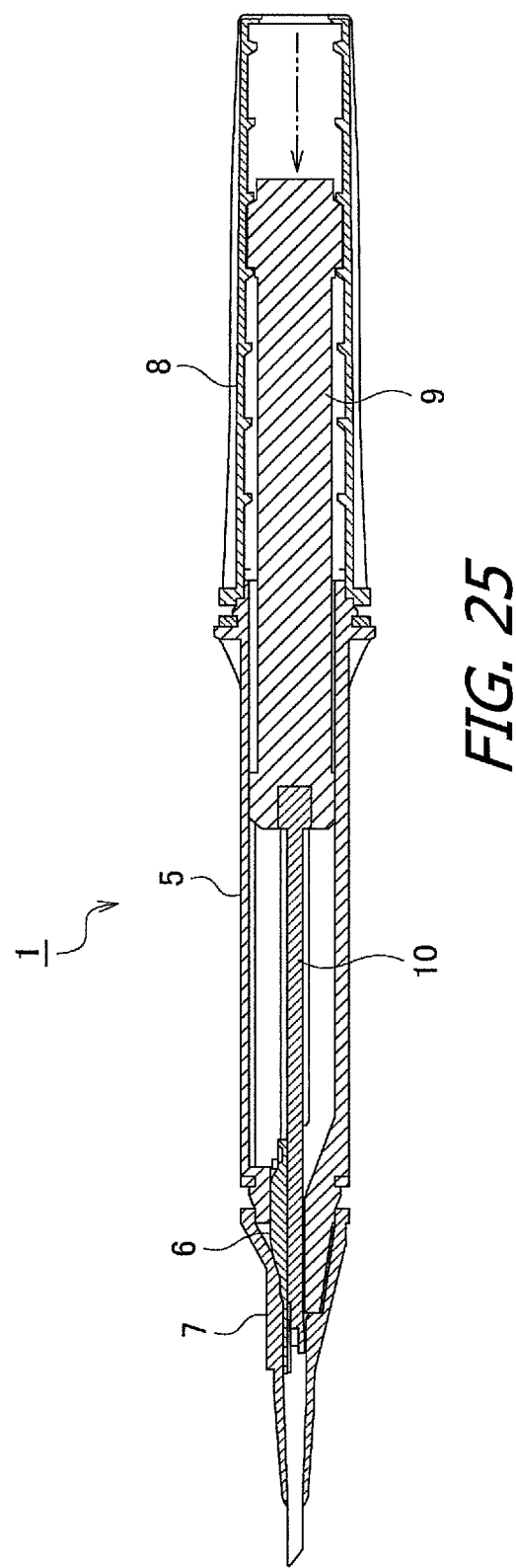
FIG. 25 is a cross-sectional view illustrating the positional relation of each portion when the screw member is rotated by one rotation from an initial state.
Figure 26:
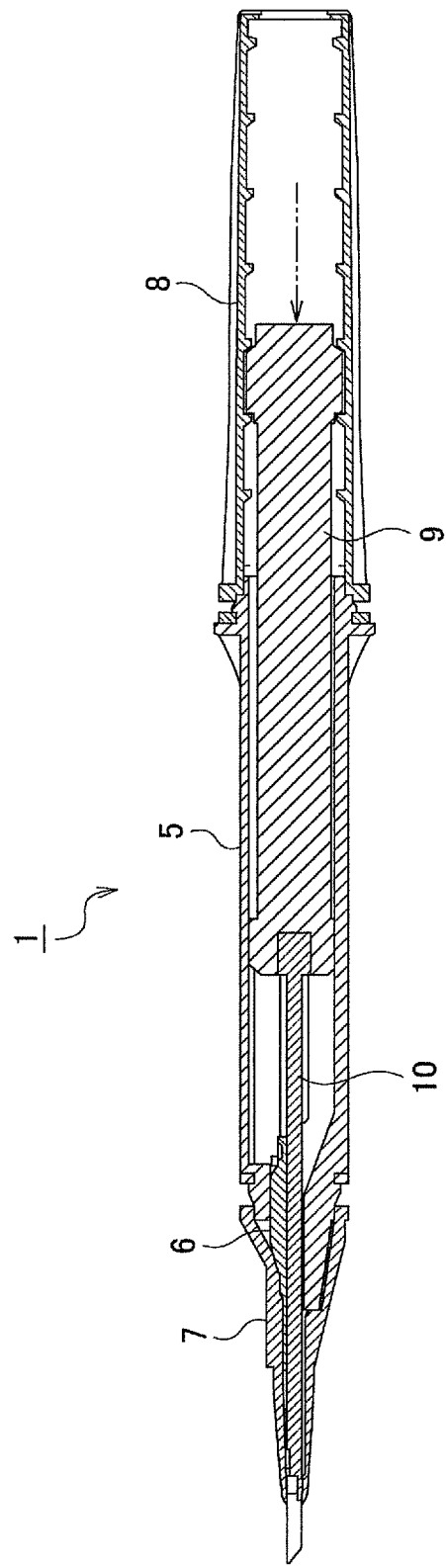
FIG. 26 is a cross-sectional view illustrating the positional relation of each portion when the screw member is rotated by two rotations from the initial state.
Figure 27:
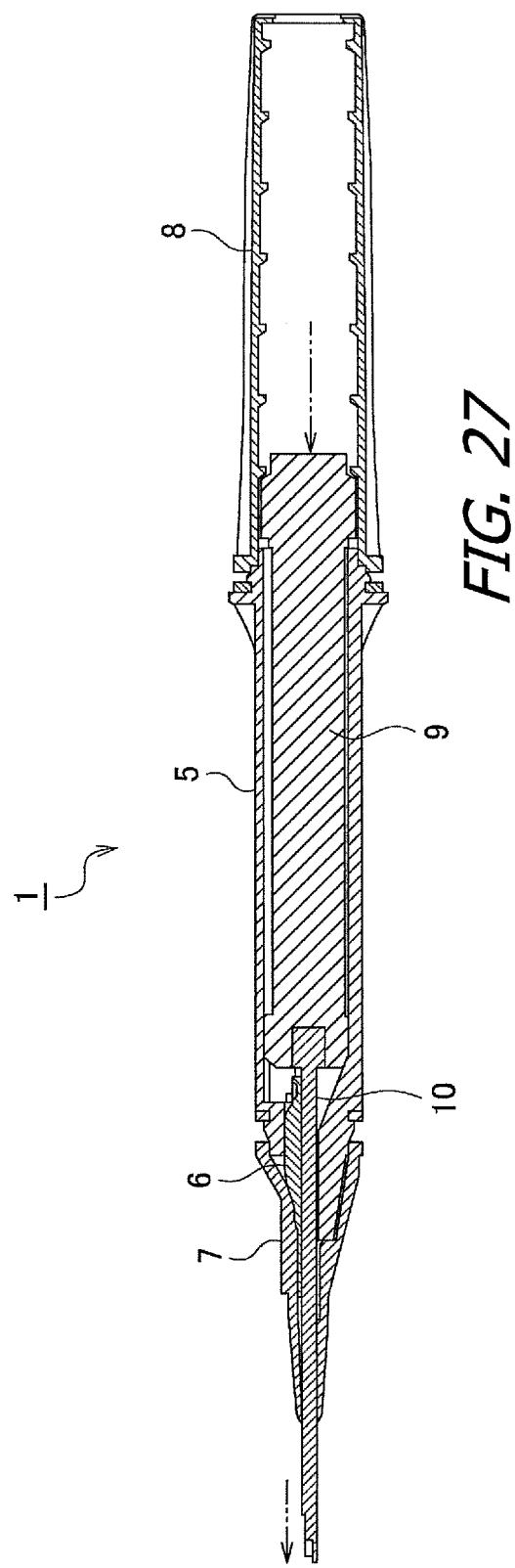
FIG. 27 is a cross-sectional view illustrating the positional relation of each portion when the screw member is rotated by three rotations from the initial state.

FIG. 23 is a cross-sectional view illustrating a positional relation of each portion before the slider is moved forward (initial state before use), and FIG. 24 is a cross-sectional view illustrating the positional relation of each portion after the slider is moved frontward. Further, FIG. 25 is a cross-sectional view illustrating the positional relation of each portion when the screw member is rotated by one rotation from the initial state, FIG. 26 is a cross-sectional view illustrating the positional relation of each portion when the screw member is rotated by two rotations from the initial state, and FIG. 27 is a cross-sectional view illustrating the positional relation of each portion when the screw member is rotated by three rotations from the initial state. In FIG. 23 to FIG. 27, signs and numerals of each member and description of the intraocular lens are omitted.

In the stage illustrated in FIG. 23, the rear end portion of the plunger 9 is disposed slightly inward (frontward) of the rear end portion of the screw member 8. Further, each member of the slider 6, the plunger 9, and the rod 10 is not protruded to outside of the hollow body which is composed of the injector body 5, the injection tube 7, and the screw member 8, excluding the wing portion 6b and the shoulder portion 6f of the slider 6. The same is applied in the stage illustrated in FIG. 24 to FIG. 26.

In the stage illustrated in FIG. 24, the intraocular lens 4 is deformed due to the advancement of the slider 6, as illustrated in FIG. 22. In the stage illustrated in FIG. 25, the tip of the rod 10 is in a state of being brought into contact with the intraocular lens 4 due to the movement of the plunger 9. In the stage illustrated in FIG. 26, the intraocular lens 4 is pushed out to the vicinity of the tip of the injection tube 7, which is the tip of the rod 10, due to the movement of the plunger 9. At this time, the intraocular lens 4 is in a small folded state, in the form in which two support portions 4b are folded back toward the optical portion 4a.

On the other hand, in the stage illustrated in FIG. 27, the tip of the rod 10 is protruded frontward from tip of the injection tube 7, due to the movement of the plunger 9. When the tip of the rod 10 is protruded from the tip of the injection tube 7, the intraocular lens 4 is released in the small folded state as described above. When the intraocular lens injector 1 is actually used, the intraocular lens 4 is released slightly before the stage illustrated in FIG. 27, specifically in the stage when the tip of the rod 10 is slightly protruded from the tip of the injection tube 7. Therefore, there is almost no change in the full length of the intraocular lens injector 1, from start to end of the operation of the intraocular lens injector 1. Further, after the slider 6 is moved frontward, the plunger 9 and the rod 10 move through the hollow body (5, 7, 8) in accordance with the rotating operation of the screw member 8. Therefore, there is almost no change in an appearance of the intraocular lens injector 1 including the relative positional relation between the injector body 5 and the screw member 8.

5. Effect of the Embodiment

According to the intraocular lens injection device 100 of the embodiments of the present invention, the following effect is obtained.

(1) In the intraocular lens injector 1, the first threaded portion 8b of the screw member 8 and the second threaded portion 9c of the plunger 9 are always engaged with each other, including the initial state before use. Therefore, there is no risk of vibration, etc., which is caused when the threaded portions are instantaneously disengaged when the screw member 8 is rotary-operated. Accordingly, generation of a defective shape or clogging, etc., of the intraocular lens 4 which is caused by the vibration, etc., during operation, is suppressed, so that the intraocular lens 4 is normally released.

(2) The intraocular lens 4 is pushed out only by the rotating operation of the screw member 8, not by a combination of the push-in operation and the rotating operation like a conventional intraocular lens injector. Therefore, the operation of the intraocular lens injector is simplified. Further, generation of the vibration, etc., during the push-in operation is prevented.

(3) There is almost no change in the full length or the appearance of the intraocular lens injector 1, from start to end of the operation of the intraocular lens injector 1. Therefore, the user is not required to pay attention to such a change, compared to a case when the full length or the appearance is changed by the push-in operation and the rotating operation by the user like the conventional intraocular lens injector. Accordingly, the user can concentrate on the tip portion of the injection tube 7 during operation of the intraocular lens injector 1.

(4) The rotary-operated screw member 8 does not move in the axial direction of the injector body 5, but the plunger 9 and the rod 10 move in the axial direction of the injector body 5 independently from the screw member 8. Therefore, even if the screw member 8 is rotary-operated, there is no change in the relative positional relation between the injector body 5 and the screw member 8 in the axial direction. Accordingly, when the user grips the injector body 5 by one hand, and performs rotating operation of the screw member 8 by the other hand, the portion for gripping the injector body 5 is not narrowed during the rotating operation. Therefore, there is no need to change the hand to grip the injector body 5 in the middle of the rotating operation of the screw member 8.

(5) When the slider 6 is moved frontward, the stopper 6g of the slider 6 is engaged with the pre-stage locking hole 13a of the injector body 5, and in this state, the reverse return of the slider 6 is prevented. Therefore, an adverse influence on the intraocular lens 4 (for example, the defective shape of the intraocular lens 4) during the reverse return of the slider 6 is prevented. Further, the misoperation of the slider 6 is prevented.

(6) When the intraocular lens injector 1 is used, only by moving the slider 6 frontward, the reverse return of the slider 6 is prevented, and simultaneously the takeout prevention state of the intraocular lens injector 1 is canceled.

6. Modified Example, Etc.

A technical range of the present invention is not limited to the abovementioned embodiments, and includes various modifications and improvements in a range that derives a specific effect obtained by features of the invention or a combination of them.

For example, in the abovementioned embodiments, a moving member is constituted by preparing the plunger 9 and the rod 10 as separate components, and connecting them. However, the plunger 9 and the rod 10 can be integrally formed by resin molding.

DESCRIPTION OF SIGNS AND NUMERALS

1 Intraocular lens injector
2 Case
3 Case cover
4 Intraocular lens
5 Injector body
6 Slider
7 Injection tube
8 Screw member
8b First threaded portion
9 Plunger
9c Second threaded portion
10 Rod
11 Lens placement portion
100 Intraocular lens injection device

The invention claimed is:

1. An intraocular lens injector, comprising:
   a hollow body having an injector body provided with a lens placement portion on which an intraocular lens is placed and an external rotating member, with a first threaded portion formed thereon, connected to a rear end portion of the injector body such that at least a portion of the external rotating member is located outside of the injector body and is rotatable around an axis of the injector body without moving in an axial direction of the injector body; and
   a moving member having a second threaded portion that is always engaged with the first threaded portion, and configured to release the intraocular lens from a tip of the hollow body by moving in an axial direction of the injector body independently from the external rotating member due to an engagement of the first threaded portion and the second threaded portion, when the external rotating member is rotary-operated.

2. The intraocular lens injector according to claim 1, wherein the moving member is housed in an interior of the hollow body without protruding from a rear end portion of the external rotating member in an initial state before use, and is configured to move in the interior of the hollow body when the external rotating member is rotary-operated.

3. The intraocular lens injector according to claim 2, having a reverse rotation prevention mechanism for preventing a reverse rotation of the external rotating member in the initial state before use.

4. The intraocular lens injector according to claim 3, comprising:
   a slider provided movably in an axial direction of the injector body, and configured to deform the intraocular lens into a prescribed shape, by abutting on the intraocular lens when moving it in one of the axial directions of the injector body; and
   a reverse return prevention mechanism configured to prevent a reverse return of the slider, when the slider is moved in one of the axial directions of the injector body.

5. The intraocular lens injector according to claim 2, comprising:
   a slider provided movably in an axial direction of the injector body, and configured to deform the intraocular lens into a prescribed shape, by abutting on the intraocular lens when moving it in one of the axial directions of the injector body; and
   a reverse return prevention mechanism configured to prevent a reverse return of the slider, when the slider is moved in one of the axial directions of the injector body.

6. The intraocular lens injector according to claim 1, having a reverse rotation prevention mechanism for preventing a reverse rotation of the external rotating member in an initial state before use.

7. The intraocular lens injector according to claim 1, wherein an intraocular lens is placed on the lens placement portion.

8. The intraocular lens injector according to claim 1, comprising:
   a slider provided movably in an axial direction of the injector body, and configured to deform the intraocular lens into a prescribed shape, by abutting on the intraocular lens when moving it in one of the axial directions of the injector body; and a reverse return prevention mechanism configured to prevent a reverse return of the slider, when the slider is moved in one of the axial directions of the injector body.

9. An intraocular lens injection device, comprising:
the intraocular lens injector of claim 8;
a case configured to house the intraocular lens injector; and
a takeout prevention mechanism configured to prevent takeout of the intraocular lens injector from the case, in a state of housing the intraocular lens injector in the case,
wherein when the slider is moved in one of the axial directions of the injector body in the state of housing the intraocular lens injector in the case, a takeout prevention state of the intraocular lens injector by the takeout prevention mechanism is canceled.

10. An intraocular lens injector, comprising:
a hollow body including an injector body, having a lens placement portion and defining a rear end portion and an axis, and a tip;
an external member, including a first threaded portion, connected to the injector body rear end portion such that at least a portion of the external member is located outside of the hollow body and the external member is rotatable around the injector body axis and is not movable in an axial direction; and
an internal member including a lens contact part and a second threaded portion that is operably connected to the lens contact part and is always engaged with the first threaded portion such that rotation of the external member results in axial movement of the internal member and movement of the lens contact part to the tip.

11. The intraocular lens injector of claim 10, wherein
the hollow body defines an interior;
the external member defines a rear end portion; and
the internal member is located within the hollow body interior, does not protrude from the external member rear end portion prior to rotation of the external member, and moves within the hollow body interior when the external member is rotated.

12. The intraocular lens injector of claim 10, wherein
the external member defines a rear end portion and the rear end portion includes an abutment;
the internal member includes a rear end; and
the external member abutment and internal member rear end are respectively configured and arranged such that the internal member rear end is prevented from moving rearwardly beyond the external member abutment.

13. The intraocular lens injector of claim 10, further comprising:
an intraocular lens on the lens placement portion.

14. The intraocular lens injector of claim 10, further comprising:

a slider, axially movable relative to the injector body, configured to deform an intraocular lens into a prescribed shape while moving in a forward axial direction.

15. The intraocular lens injector of claim 14, wherein
the injector body includes an aperture;
the slider includes a stopper that enters the aperture in response to movement of the slider in the forward axial direction; and
the aperture and the stopper are respectively configured such that the slider may not be moved in a rearward axial direction when the stopper is in the aperture.

16. The intraocular lens injector system, comprising:
the intraocular lens injector of claim 14; and
a case configured to house the intraocular lens injector and including a recess configured to receive a portion of the slider in such a manner that removal of the intraocular lens injector from the case is prevented when the slider is in a first position and removal of the intraocular lens injector from the case is permitted when the slider is in a second position.

17. An intraocular lens injector, comprising:
a hollow body including an injector body, having a lens placement portion and defining a rear end and an axis, and a tip;
an external member, including a first threaded portion, mounted on the injector body rear end such that the external member is rotatable around the injector body axis and is not movable in an axial direction; and
an internal member including a lens contact part and a second threaded portion that is operably connected to the lens contact part and is always engaged with the first threaded portion such that rotation of the external member results in axial movement of the internal member and movement of the lens contact part to the tip.

18. The intraocular lens injector of claim 17, wherein
the hollow body defines an interior;
the external member defines a rear end portion; and
the internal member is located within the hollow body interior, does not protrude from the external member rear end portion prior to rotation of the external member, and moves within the hollow body interior when the external member is rotated.

19. The intraocular lens injector of claim 17, wherein
the external member defines a rear end portion and the rear end portion includes an abutment;
the internal member includes a rear end; and
the external member abutment and internal member rear end are respectively configured and arranged such that the internal member rear end is prevented from moving rearwardly beyond the external member abutment.

20. The intraocular lens injector of claim 17, further comprising:
a slider, axially movable relative to the injector body, configured to deform an intraocular lens into a prescribed shape while moving in a forward axial direction.

* * * * *